(12) United States Patent
Wang et al.

(10) Patent No.: US 11,191,518 B2
(45) Date of Patent: Dec. 7, 2021

(54) ULTRASOUND SYSTEM AND METHOD FOR DETECTING LUNG SLIDING

(71) Applicant: KONINKLIJKE PHILIPS N.V., Eindhoven (NL)

(72) Inventors: Shougang Wang, Cambridge, MA (US); Balasudar Iyyavu Raju, North Andover, MA (US); Jingping Xu, Shanghai (CN); Anthony M. Gades, Bothell, WA (US); McKee Dunn Poland, Andover, MA (US); Shiwei Zhou, Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 254 days.

(21) Appl. No.: 16/086,729

(22) PCT Filed: Mar. 24, 2017

(86) PCT No.: PCT/EP2017/057096
§ 371 (c)(1),
(2) Date: Sep. 20, 2018

(87) PCT Pub. No.: WO2017/162860
PCT Pub. Date: Sep. 28, 2017

(65) Prior Publication Data
US 2019/0105013 A1    Apr. 11, 2019

(30) Foreign Application Priority Data

Mar. 24, 2016 (WO) ................ PCT/CN2016/077242
Jul. 14, 2016 (EP) .................................... 16179452

(51) Int. Cl.
*A61B 8/00* (2006.01)
*A61B 8/08* (2006.01)
(Continued)

(52) U.S. Cl.
CPC .............. *A61B 8/08* (2013.01); *A61B 8/0858* (2013.01); *A61B 8/463* (2013.01); *A61B 8/469* (2013.01);
(Continued)

(58) Field of Classification Search
CPC ......... A61B 8/08; A61B 8/0858; A61B 8/463; A61B 8/469; A61B 8/5207; A61B 8/5223;
(Continued)

(56) References Cited

U.S. PATENT DOCUMENTS 6,283,919 B1    9/2001 Roundhill et al.
6,458,083 B1    10/2002 Jago et al.
(Continued)

FOREIGN PATENT DOCUMENTS

WO    2008073560 A2    6/2008
WO    2015048767 A2    4/2015
(Continued)

OTHER PUBLICATIONS

Luna et al "How I Do It: Lung Ultrasound" Cardiovascular Ultrasound 2014, vol. 12 p. 25.
(Continued)

*Primary Examiner* — Mark D Remaly

(57) ABSTRACT

The present invention proposes an ultrasound system and a method of detecting lung sliding on the basis of a temporal sequence of ultrasound data frames of a first region of interest. The first region of interest includes a pleural interface of a lung. A sub-region identifier (410) is configured to identify, for each of the ultrasound data frames, a sub-region of a scanned region of the ultrasound data frame, the sub-region comprising at least part of the pleural interface; a lung sliding detector (420) is configured to derive a parametric map for the sub-region on the basis of at least two
(Continued)

ultrasound data frames of the temporal sequence, parametric values of the parametric map indicating a degree of tissue motion over the at least two ultrasound frames; wherein the lung sliding detector is further configured to extract data of the sub-regions from the at least two ultrasound data frames, and to derive the parametric map on the basis of the extracted data.

16 Claims, 16 Drawing Sheets

(51) Int. Cl.
  *G06T 7/246* (2017.01)
  *G06T 7/215* (2017.01)
  *G06T 7/13* (2017.01)
  *G06T 7/00* (2017.01)
(52) U.S. Cl.
  CPC .......... *A61B 8/5223* (2013.01); *A61B 8/5246* (2013.01); *G06T 7/0016* (2013.01); *G06T 7/13* (2017.01); *G06T 7/215* (2017.01); *G06T 7/246* (2017.01); *A61B 8/5207* (2013.01); *A61B 8/5276* (2013.01); *G06T 2207/10016* (2013.01); *G06T 2207/10132* (2013.01); *G06T 2207/20104* (2013.01); *G06T 2207/30061* (2013.01); *G06T 2207/30064* (2013.01)
(58) Field of Classification Search
  CPC ................ A61B 8/5246; A61B 8/5276; G06T 2207/10016; G06T 2207/10132; G06T 2207/20104; G06T 2207/30061; G06T 2207/30064; G06T 7/0016; G06T 7/13; G06T 7/215; G06T 7/246; G16H 50/30
  See application file for complete search history.

(56) References Cited

U.S. PATENT DOCUMENTS

| 8,343,053 | B2 | 1/2013 | Feng et al. |
| 8,914,097 | B2 | 12/2014 | Burlina et al. |
| 2007/0167771 | A1 | 7/2007 | Ostad |
| 2013/0184584 | A1 | 7/2013 | Berkey |
| 2013/0197370 | A1 | 8/2013 | Burlina et al. |
| 2015/0065849 | A1 | 3/2015 | Berlina et al. |
| 2017/0273659 | A1* | 9/2017 | Xu .......................... G06T 7/194 |

FOREIGN PATENT DOCUMENTS

| WO | 2015113806 A1 | 8/2015 |
| WO | 2016046140 A1 | 3/2016 |
| WO | 2017046692 A1 | 3/2017 |

OTHER PUBLICATIONS

Perera et al "Rapid Ultrasound in Shock: The Rush Protocol" Emergency Medicine, Apr. 2010, vol. 2010, p. 12-26.

Ramin et al "Novel Automatic Detection of Pleura and B-Lines (Comet-Tail Artifacts) on in Vivo Lung Ultrasound Scans" Progress in Biomedical Optics and Imaging, SPIE vol. 9790, Apr. 1, 2016, p. 97900.

K. L. Anderson, et. al., 'Inter-Rater Reliability of Quantifying Pleural B-Lines Using Multiple Counting Methods', J Ultrasound Med, 2013, vol. 32:115-120.

W.C. Manson, et. al., 'Identification of Sonographic B-lines with Linear Transducer Predicts Elevated B-Type Natriuretic Peptide Level', West J Emerg Med, 2011, vol. 12: 102-106.

R. Copetti, et. al., 'Chest sonography: a useful tool to differentiate acute cardiogenic pulmonary edema from acute respiratory distress syndrome', Cardiovascular Ultrasound, 2008, vol. 6: 16.

A. R. McLean, et. al., 'Ultrasound determination of chest wall thickness: implications for needle thoracostomy', The American Journal of Emergency Medicine, 2011, vol. 29:1173-1177.

C. F.Dietrich, et. al., 'Ultrasound of the pleurae and lung', Ultrasound in Med. & Biol, 2015, vol. 41(2):351-365.

Alrajhi et al.: "Test Characteristics of Ultrasounography for the Detection of Pneumothorxasystematic Reviewand Meta-Analyis"; CHEST 2012, pp. 141-708.

Ku et al.: "Clinician-Performed Beside Ultrasound for the Diagnosis of Traumatic Pneumothorx"; Western Journal of Emergency Medicine, vol. XIV, No.2, Mar. 2013, pp. 103-108.

Volpicelli" Sonographic Diagnosis of Pneumothorax"; Intensive Care Med (2011), vol. 37, pp. 224-232.

* cited by examiner

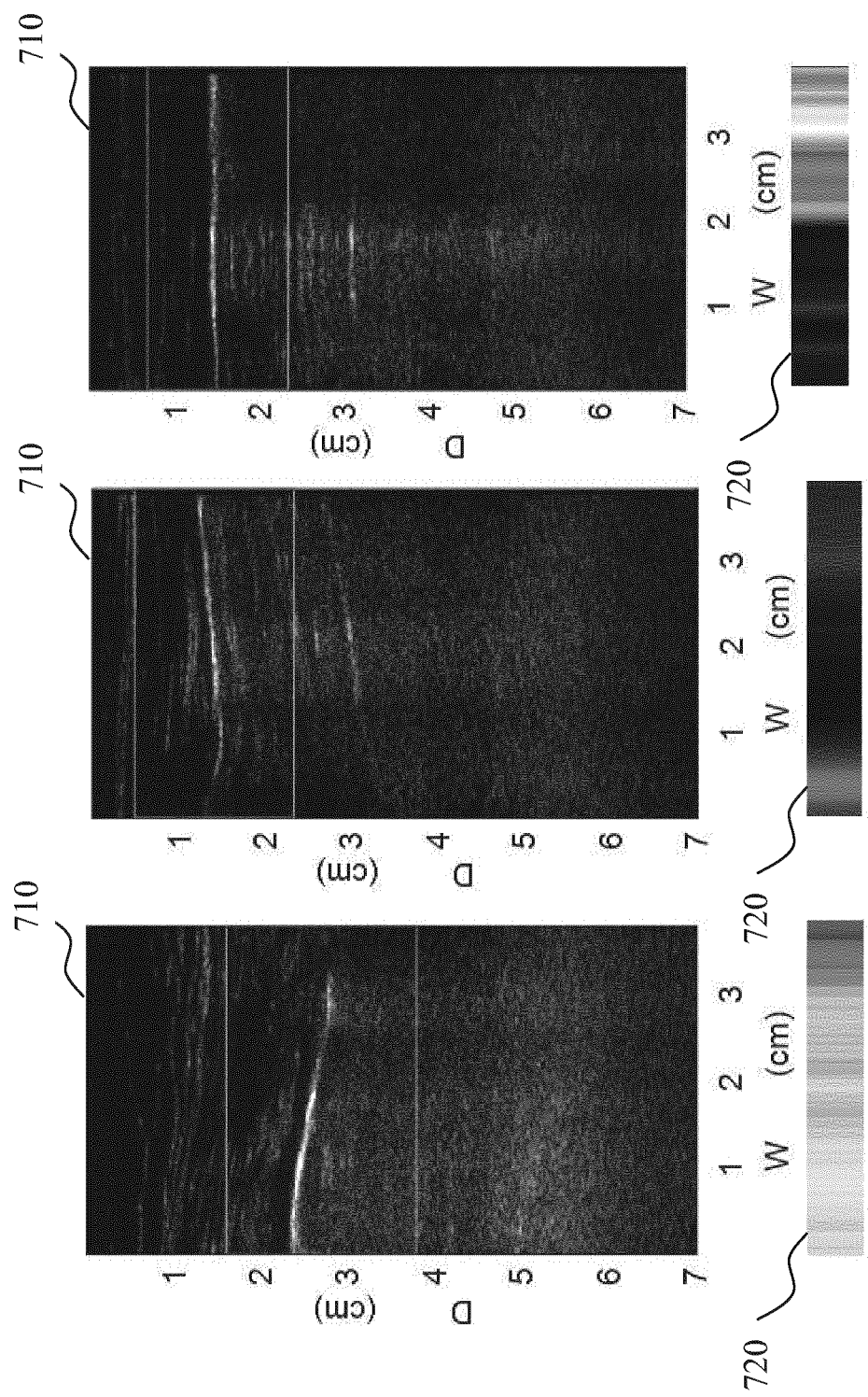

ULTRASOUND SYSTEM AND METHOD FOR DETECTING LUNG SLIDING

This application is the U.S. National Phase application under 35 U.S.C. § 371 of International Application No. PCT/EP2017/057096 filed on Mar. 24, 2017, which claims the benefit of PCT/CN2016/077242 filed Mar. 24, 2016 and EP 16179452.4 filed Jul. 14, 2016. These applications are hereby incorporated by reference herein.

FIELD OF THE INVENTION

The present invention relates to an ultrasound system and a method for detecting a lung sliding motion, particularly a lung sliding motion on the basis of a temporal sequence of ultrasound B-mode frames of a region of interest including a pleural interface of a lung.

BACKGROUND OF THE INVENTION

Pneumothorax (PTX) is a commonly encountered condition in the emergency room, the intensity or intensive care unit (ICU), and the critical care unit (CCU). Ultrasound imaging using the eFAST protocol (extended Focused Assessment with Sonography on Trauma) is used for the assessment of PTX. Expert consensus has led to the development of the simplified BLUE (Bedside Lung Ultrasound Examination) protocol where certain features such as Lung sliding, B-lines, lung point, lung pulse are evaluated to determine the presence or absence of PTX.

It is known from literature that when well-trained experts evaluate the lung, the sensitivity of PTX detection is around 92%, whereas for emergency room (ER) doctors with the minimum required training it is only about 57%. Chest X-ray (CXR) has also been shown to have poor accuracy. While CT is the gold standard, it is not always available, cannot be performed on unstable patients, and has radiation concerns. Thus, a more automated method to detect PTX using ultrasound would be useful in early detection and improved care to the patient.

In rural and emerging markets, the current adoption of ultrasound, especially in non-traditional medical departments such as the emergency department and ICU/CCU etc., continues to be particularly low mainly due to lack of training and experience in the ER community. In contrast, patient throughput in such departments is high, making a high demand on user-independent and robust methods for trauma identification, especially for chest trauma. In China in particular, most ER scans are performed by junior ultrasound doctors who lack training in emergency and critical care ultrasound but who have experience in general ultrasound imaging, and eFAST protocols have not yet been institutionalized. Automated methods are expected to provide assistance and guidance to such users; they will minimize the amount of training needed and lead to better adoption of ultrasound in the ER, the ICU/CCU, and/or any other medical department.

US2013/197370 A1 describes a method of determining the presence of a pneumothorax includes obtaining a series of frames of image data relating to a region of interest including a pleural interface of a lung.

WO2016/046140A1 discloses an ultrasound system comprising a probe configured to obtain ultrasound data relating to a scanning region including at least part of a pleural interface of a lung and a data analyzer configured to automatically detect information for determining lung sliding and/or lung point using one or more cross correlation maps derived from the data.

SUMMARY OF THE INVENTION

Therefore, it would be advantageous to provide an ultrasound system and method capable of deriving and presenting quantitative and/or qualitative information so as to facilitate understanding and/or interpretation of ultrasound data of the lung region. It would be also advantageous to provide an ultrasound system and method for detecting lung sliding and/or lung point.

In accordance with an embodiment of a first aspect of the present invention, there is proposed an apparatus for detecting lung sliding on the basis of a temporal sequence of ultrasound data frames of a first region of interest. The apparatus comprises a sub-region identifier configured to identify, for each of the ultrasound data frames, a sub-region of a scanned region of the ultrasound data frame, the sub-region comprising at least part of the pleural interface; a lung sliding detector configured to derive a parametric map for the sub-region on the basis of at least two ultrasound data frames of the temporal sequence, parametric values of the parametric map indicating a degree of tissue motion over the at least two ultrasound frames; wherein the lung sliding detector is further configured to extract data of the sub-regions from the at least two ultrasound data frames, and to derive the parametric map on the basis of the extracted data.

In some embodiments, the apparatus is part of an ultrasound device or system capable of acquiring, via an ultrasound probe, ultrasound data. Additionally or alternatively, the apparatus is connectable to one or more storage devices for storing ultrasound data, which may be the storage device of a PACS (picture archiving and communication system) or hospital information system.

An ultrasound data frame is acquired by receiving ultrasound echo signals from a region, and such a region is often called the scanned region or the imaged region. The scanned region can be two-dimensional or three-dimensional. An ultrasound data frame for a two-dimensional scan region can be directly acquired by a two-dimensional scan, or can be reconstructed from ultrasound data of a three-dimensional scan. Each ultrasound data frame of the temporal sequence comprises ultrasound data of the first region of interest at a different time point or instant, and thus, the scanned region of each ultrasound data frame is intended to be the same, namely the first region of interest. However, the scanned region of each ultrasound data frame may be different in practice due to, for example, probe movements. Further, even if the scanned region in each ultrasound data frame is the same, the same tissue in the first region of interest may not appear at the same pixel location in each ultrasound data frame due to, for example, tissue movements inside the scanned region.

The ultrasound data frame can be a B-mode data frame or any other suitable ultrasound data frame in which each value represents the amplitude or intensity of the echo. The temporal sequence of the ultrasound data frames can be a B-mode video, also called B-mode cine-loop. The ultrasound data frame can, for example, be stored and transferred in the format of DICOM (digital imaging and communications in Medicine) data. Alternatively, the ultrasound data frame can be an ultrasound radio frequency (RF) data frame, or any other suitable ultrasound data frame derived from the ultrasound radio frequency data frame. The ultrasound radio frequency data frame typically has a higher axial resolution.

In this case, the parametric map can be derived directly from the ultrasound radio frequency data frame, by for example calculating the frame-to-frame phase difference, and alternatively, B-mode data frames are derived first from the ultrasound radio frequency data frames and then the parametric map is derived from the B-mode data frames.

The derived parametric map indicates the degree of tissue motion, and thus can facilitate the users to interpret the ultrasound data, especially to identify tissue motion. Taking PTX evaluation as an example, currently, clinicians such as doctors and/or sonographers use their considerable training to determine a lung sliding and/or lung point feature on black and white B-mode cine-loops. In emergency situations this process adds to the time and effort involved, while the clinician is trying to perform multiple critical tasks. Moreover, it is difficult to manually identify subtle motion features such as lung sliding compared to strong background motion by visually observing the ultrasound B mode videos, especially when the lung sliding is reduced. The derived parametric map quantitatively represents the degree of tissue motion, and thus can facilitate the clinicians to identify the existence of lung sliding and/or lung point.

Furthermore, the inventors of the present invention have proposed to identify first a sub-region of the scanned region, such as a region around the pleural interface, and then derive the parametric map only for the sub-region, rather than the whole scanned region, on the basis of the following recognitions. The inventors have recognized that tissue motion around the pleural interface may be more important for the detection of lung sliding and/or lung point, the parametric map for the whole scanned region contains more information than necessary, and the unnecessary information, such as tissue motion other than lung motion, may de-focus the users. Furthermore, the computational complexity can be significantly reduced by restricting the derivation of the parametric map in a sub-region of the scanned region, which is very attractive especially for mobile ultrasound applications where such derivation is implemented in a portable device. The portable device can be a tablet such as a PAD or a smart phone.

In accordance with some embodiments, the apparatus further comprises a user interface configured to visualize the likelihood of lung sliding on the basis of the derived parametric map. The visualization can be achieved in different ways in various embodiments.

In one embodiment, the user interface is configured to present at least part of the derived parametric map in the form of a parametric image, overlaid with an image of at least the sub-region generated on the basis of at least one of the ultrasound data frames of the sequence. The parametric image can represent the whole parametric map. Alternatively, the parametric image can represent part of the parametric map, such as the parametric map for the region below the pleural line. The image overlaying the parametric image can, for example, be a B-mode image. The image overlaying the parametric image can be generated on the basis of a single ultrasound data frame of the temporal sequence, and alternatively, it can be generated on the basis of more than one ultrasound data frames by, for example, averaging across the more than one ultrasound data frames. The image overlaying the parametric image can be an image of the whole scanned region of the ultrasound data frame(s), or alternatively, it can be an image of a part of the scanned region of the ultrasound data frame(s) which comprises the sub-region. Through visually observing the parametric image, the users can observe tissue motion in the region around the pleural interface in a more straightforward way, and can thus identify the existence of lung sliding and/or lung point faster and more reliably.

Additionally or alternatively, the user interface is configured to visualize the likelihood of lung sliding in the form of a strip. In particular, the lung sliding detector is further configured to derive, on the basis of the parametric map, a sliding profile representing sliding values as a function of lateral positions, each sliding value for a lateral position indicating the likelihood of lung sliding at the lateral position; and the user interface is further configured to present the derived sliding profile in the format of a strip, overlaid with or next to an image of at least the sub-region generated on the basis of at least one of the ultrasound data frames of the sequence. The likelihood of lung sliding at a lateral position is proportional to the extent or severity of tissue motion around the pleural interface at that lateral position. The more tissue motion at a lateral position, the higher the likelihood of lung sliding at the lateral position is. Typically, lung sliding appears along the whole pleural line for a normal lung, may disappear under PTX conditions, and may partially disappear at the boundary of the PTX (known as lung point), meaning that it exists at certain lateral positions while it does not exist at other lateral positions, under partial PTX conditions. Through visually observing the strip, the users can directly observe the likelihood of lung sliding at individual lateral positions, and identify the lung point when determining the boundary of the PTX under partial PTX conditions.

In accordance with some embodiments, the user interface is further configured to receive a user input for indicating a modification of a grayscale-coding or color-coding scheme, and to modify the visualization on the basis of the received user input. The user interface is configured to visualize the likelihood of lung sliding in accordance with a grayscale-coding or color-coding scheme. For example, the aforementioned parametric image and/or strip can be grayscale-coded or color-coded. The user interface is further configured to receive a user input for indicating a modification of the grayscale-coding or color-coding scheme, and to modify the visualization on the basis of the received user input. In one embodiment, the user interface comprises a touchscreen and displays a bar, slider or the like representing the grayscale-coding or color-coding scheme, and the user can modify the grayscale-coding or color-coding scheme by manipulating the bar, the slider or the like.

In accordance with some embodiments, the apparatus further comprises a user interface configured to receive a user input for indicating a modification to the identified sub-region; and the sub-region identifier is configured to modify the identified sub-region on the basis of the received user input. Thus, the user is able to manually trim and/or move the identified sub-region, which is particularly useful for the cases where the automatic identification of the sub-region fails to identify the region around the pleural interface as the sub-region. In one embodiment, the user interface comprises a touchscreen. The touchscreen allows the user to perform various operations through physical contact and interaction, such as touch or tap, drag and drop, touch flow, multi-touch and/or other physical interaction. In an embodiment, the sub-region identifier is configured to modify, including move and/or resize, the identified sub-region on the basis of one or more operations applied in the displayed sub-region on the touch screen.

The sub-region identifier can be configured to identify the sub-region in different ways in accordance with various embodiments.

In some embodiments, the sub-region is identified on the basis of one or more predetermined parameters. The one or more predetermined parameters can be set by default, by user selection, or they can be derived on the basis of other parameters. In an example, the one or more predetermined parameters comprise a predetermined depth range, and the sub-region is identified as part of the scanned region within the predetermined depth range. Based on the observation that the pleural interface is typically about 1.5-5 cm under the skin surface from the top of the scanned region, the predetermined depth range can be set as 0-6 or 1-6 cm for example. Based on the observation that the depth of the pleural interface increases with the BMI (body mass index) of the subject, the predetermined depth range can be adjusted on the basis of the BMI of the subject. Based on the observation that the pleural interface is approximately 0.5 cm below the ribs, the predetermined depth range can be set on the basis of the depth of the rib(s).

In some other embodiments, the apparatus further comprises a pleural line detector configured to detect a pleural line in at least one of the ultrasound data frames, and the sub-region identifier is configured to identify the sub-region for each of the ultrasound data frames on the basis of the detected pleural line. As is well-known, the pleural interface appears as an echogenic horizontal line, called a pleural line, due to strong reflection at the pleural interface. Once the pleural line is automatically detected in an ultrasound data frame, the sub-region in that ultrasound image can be identified as surrounding the detected pleural line. In an example, the top and bottom edges of an identified sub-region are respectively above and below the detected pleural line by a predetermined depth value, such as 0.5 cm. The depth of the pleural line typically varies from 1.5-5 cm from one subject to another. By knowing the location of the pleural line for the subject under examination, a smaller sub-region can be identified. In one example, the pleural line is detected in each of the ultrasound data frames, and then the sub-region in each ultrasound data frame is identified on the basis of the detected pleural line in that ultrasound data frame. Alternatively, the sub-region identifier is configured to detect the pleural line and the sub-region in one ultrasound data frame, and then identify the sub-region in each of other ultrasound data frames by assuming that the spatial location of the sub-region is the same for all the ultrasound data frames. In this case, a relatively large sub-region can be identified so as to provide sufficient tolerance for possible motion across the ultrasound data frames.

The automatic detection of the pleural line can be implemented by any suitable existing and future-developed detection algorithm. In accordance with one embodiment, the pleural line detector is configured to estimate a depth of the pleural interface, and detect a pleural line in at least one of the ultrasound data frames of the temporal sequence on the basis of the estimated depth. As compared to those detection algorithms which search the pleural line throughout the scanned region, it is proposed to search or detect the pleural line on the basis of the estimated depth of the pleural line, resulting in a faster and more reliable detection.

The depth of the pleural can be estimated in different ways.

In some embodiments, estimating the depth of the pleural interface comprises: deriving, for each of one or more predetermined lateral positions, an intensity profile representing an intensity value as a function of depth, each intensity value indicating an averaged ultrasound data value at the corresponding depth over multiple ultrasound data frames of the temporal sequence, on the basis of the multiple ultrasound data frames of the temporal sequence, and estimating the depth of the pleural interface on the basis of the derived intensity profile(s). In this way, the depth of the pleural line is estimated on the basis of multiple frames rather than a single frame, and thus the estimated depth of the pleural line is more reliable, especially when the pleural line in a certain frame is difficult to detect. For example, the pleural line in a certain frame is not a continuous bright horizontal line, but is broken into several lines, and is therefore difficult to be distinguished from other bright lines in the scanned region. Lateral positions refer to multiple points along the lateral direction or surface which is orthogonal to the depth direction. For example, the one or more predetermined lateral positions can comprise a center position along the lateral direction and/or two positions apart from the center position by a predetermined distance, such as one-fourth of the width of the scanned region. In some embodiments, the depth of the pleural interface is estimated as the depth of the peak of the intensity profiles. In some embodiments, when more than one intensity profiles are derived, the depth of the pleural interface can be estimated as an average of the depth of the peak of each intensity profile.

In some other embodiments, estimating the depth of the pleural interface comprises: receiving an ultrasound data frame of a second region of interest including a pleural interface of the lung and at least one rib, the second region of interest being a transverse view of the lung; estimating a depth of the at least one rib on the basis of the ultrasound data frame; and estimating the depth of the pleural interface on the basis of the estimated depth of the at least one rib and a predetermined value. The pleural line consists of the closely opposed visceral and parietal pleura. In a normal lung, the visceral pleura slides horizontally against the parietal pleura, producing a phenomenon called "lung sliding". Thus, the detection of the degree of tissue motion is useful for the detection of lung sliding. The lung sliding detector can be configured to derive the parametric map for indicating the degree of tissue motion in various ways.

In some embodiments, the parametric value can be derived by estimating the motion vector by performing block correlation or normalized cross correlation, or by calculating optical flow vectors. Due to tissue motion, the same tissue point may appear at different pixel locations in different ultrasound data frames. The distance over which the same tissue point moves can be used to represent the degree of the tissue motion. The aforementioned algorithms are intended to determine the motion of individual tissue points so as to assess the degree of the tissue motion.

The inventors of the present invention have observed and recognized that in the case of lung sliding, the ultrasound data above the pleural line is a structured tissue-reflection which is real and which is trackable by estimating the motion vector, and the ultrasound data below the pleural line contains a lot of artefacts which do not reflect any real structure of body tissue for normal lungs, and the estimated motion vector is not reliable. The inventors of the present invention have thus proposed to measure a single-pixel intensity-change over time caused by tissue motion, rather than estimating the motion vector of the tissue motion. In particular, the parametric value for a pixel location in the scanned region indicates, and is for example proportional to, an amount of change in ultrasound data values of the pixel location over the at least two ultrasound data frames as a result of tissue motion.

In accordance with some embodiments, the apparatus further comprises a background motion detector configured to detect a degree of background motion and determine whether the degree of background motion exceeds a predetermined threshold; and a user interface configured to present the derived parametric map only if the degree of background motion does not exceed the predetermined threshold, and/or to present an indicator for indicating the degree of background motion if the degree of background motion exceeds the predetermined threshold. Background motion is known to be typically caused by probe motion, breathing, internal muscle movement are typical background motions, and the existence of the background motion may negatively impact the detection of lung sliding. In an embodiment, the degree of background motion is determined on the basis of the derived parametric map. The background motion may be determined in other ways, such as by means of any motion detection algorithm or an additional sensor provided on the probe etc. Preferably, in accordance with an embodiment of the invention, the degree of background motion is measured by an average of the parametric values above the pleural line. Typically, the B-mode values of pixels above the pleural line are higher. The inventors of the present invention have recognized that if there is background motion, all pixel values may change due to the motion, but the value change of darker pixels is smaller than the value change of brighter pixels, and therefore, it is advantageous to average the parametric values of the brighter pixels.

In accordance with an embodiment of a second aspect of the present invention, there is proposed an ultrasound system. The ultrasound system comprises: an ultrasound data acquisition unit comprising an ultrasound transducer array, configured to acquire a temporal sequence of ultrasound data frames of a first region of interest including a pleural interface of a lung; and a data processor for processing the temporal sequence, configured to identify, for each of the ultrasound data frames, a sub-region of a scanned region of the ultrasound data frame, the sub-region comprising at least part of the pleural interface, to extract data of the sub-regions from the at least two ultrasound data frames, and to derive a parametric map for the sub-region on the basis of the extracted data, parametric values of the parametric map indicating tissue motion over the at least two ultrasound frames.

In accordance with an embodiment of a third aspect of the present invention, there is proposed a method of detecting lung sliding. The method comprises the steps of: retrieving a temporal sequence of ultrasound data frames of a first region of interest including a pleural interface of a lung; identifying, for each of the ultrasound data frames, a sub-region of the scanned region of the ultrasound data frames, the sub-region comprising at least part of the pleural interface; extracting data of the sub-regions from the at least two ultrasound data frames; and deriving a parametric map for the sub-region on the basis of the extracted data, parametric values of the parametric map indicating tissue motion over the at least two ultrasound frames.

In accordance with an embodiment of a fourth aspect of the present invention, there is proposed a computer product comprising computer program instructions which, when being executed, perform the aforementioned method.

Other objects and advantages of the present invention will become more apparent and can be easily understood with reference to the description made in combination with the accompanying drawings.

DESCRIPTION OF THE DRAWINGS

The present invention will be described and explained hereinafter in more detail in combination with embodiments and with reference to the drawings, wherein:

FIGS. 6A-6C each illustrate an ultrasound B-mode image and a combined image of the ultrasound B-mode image overlaid with a parametric map in accordance with an embodiment of the present invention, wherein FIG. 6A illustrates a case where lung sliding is present, FIG. 6B illustrates a case where lung sliding is absent, and FIG. 6C illustrates a case where lung sliding is partially present and a lung point is present(?);

FIGS. 7A-7C each illustrate a combined image of an ultrasound B-mode image and a horizontal strip for indicating the likelihood of lung sliding in accordance with an embodiment of the present invention, wherein FIG. 7A illustrates a case where lung sliding is present, FIG. 7B illustrates a case where lung sliding is absent, and FIG. 7C illustrates a case where lung sliding is partially present and a lung point is present;

Figure 1:
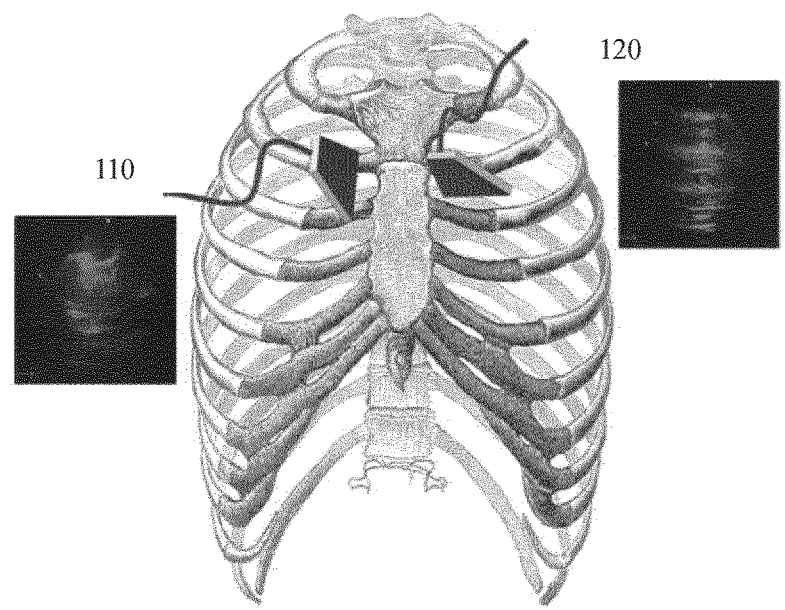
FIG. 1 illustrates two typical scans, namely a longitudinal scan and an oblique scan for a lung.

The same reference signs in the figures indicate similar or corresponding features and/or functionalities.

DETAILED DESCRIPTION OF THE EMBODIMENTS

The present invention will be described with respect to particular embodiments and with reference to certain drawings, but the invention is not limited thereto but only by the claims. The drawings described are only schematic and are non-limiting. In the drawings, the size of some of the elements may be exaggerated and not drawn to scale for illustrative purposes.

FIG. 1 illustrates two typical scans, namely a longitudinal scan and an oblique scan for a lung (G. Luna and G. Volpocelli, 'How I do it: Lung ultrasound', Cardiovascular Ultrasound, 2014, Vol. 12:25). Referring to FIG. 1, lung ultrasound (LUS) can be performed on the whole chest by positioning the ultrasound transducer both longitudinally, perpendicular to the ribs, and obliquely, along the intercostal spaces, which are referred to as a longitudinal scan 110 and an oblique scan 120, respectively.

Figure 2:
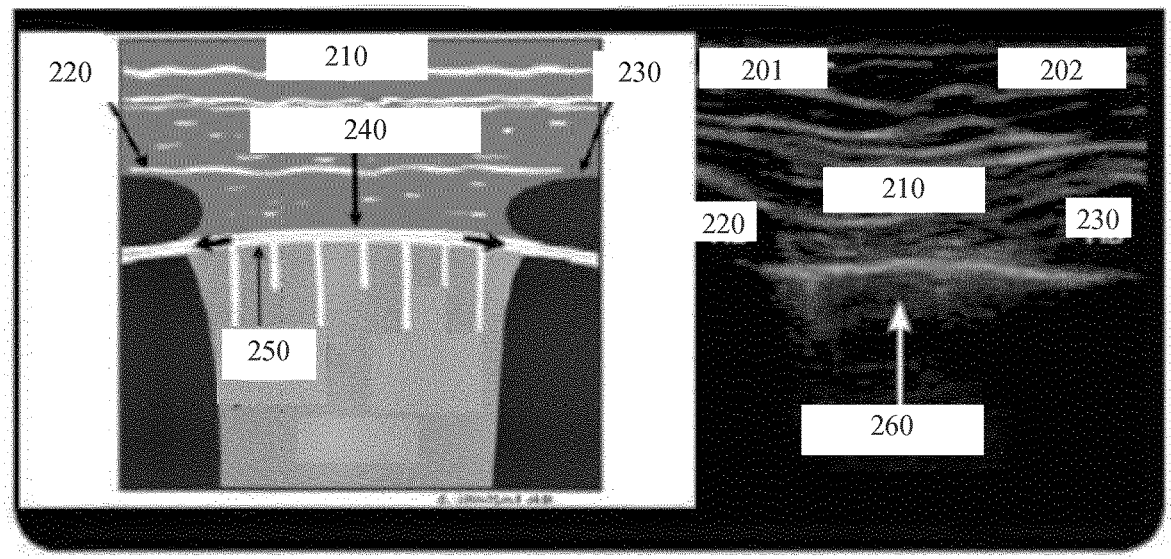
FIG. 2 illustrates the lung sliding phenomenon in a schematic drawing and an ultrasound B-mode image.

FIG. 2 illustrates the lung sliding phenomenon in a schematic drawing and an ultrasound B-mode image (Philips Perera, et. al, 'Rapid ultrasound in shock: The RUSH protocol', Emergency Medicine, April 2010, Volume 2010: 12-26).

PTX represents the second most common injury, after rib fracture, in blunt and penetrating chest trauma cases and can be detected on ultrasound using four lung features including lung sliding, B-lines, lung point and lung pulse. Small PTXs are usually asymptomatic and can safely be managed without a chest drain, but emergency physicians need to pay more attention to their progress. In cases where the pneumothorax is due to blunt or penetrating trauma, any size PTX should be treated with a thoracotomy tube to avoid the creation of a tension PTX. Large PTXs may cause respiratory distress, and tension PTXs can cause cardiorespiratory failure.

Lung sliding is the dynamic horizontal movement of the pleural line during respiration in an intact lung. FIG. 2 illustrates a schematic drawing of a lung on the left, and a corresponding ultrasound B-mode image on the right. Referring to FIG. 2, a superior rib 220 and an inferior rib 230 appear beneath the chest wall 210 at the superior side 201 and the inferior side 202, and dark regions appear right beneath the ribs due to the strong reflection of the ribs and are referred to as rib shadowing. The pleural interface appears as an echogenic horizontal line 260 (called pleural line) due to strong reflection at the pleural interface, located approximately a half centimeter posterior to the ribs 220, 230. The pleural interface consists of the closely opposed visceral pleura 250 and parietal pleura 240. In a normal lung, the visceral pleura 250 slides horizontally against the parietal pleura 240, producing a phenomenon called lung sliding, with a glistening or shimmering appearance as the subject breathes. Under a pneumothorax condition, the aforementioned lung sliding phenomenon will disappear due to air leaking into the chamber of the rib case and stopping the penetration of ultrasound waves.

Figure 3:
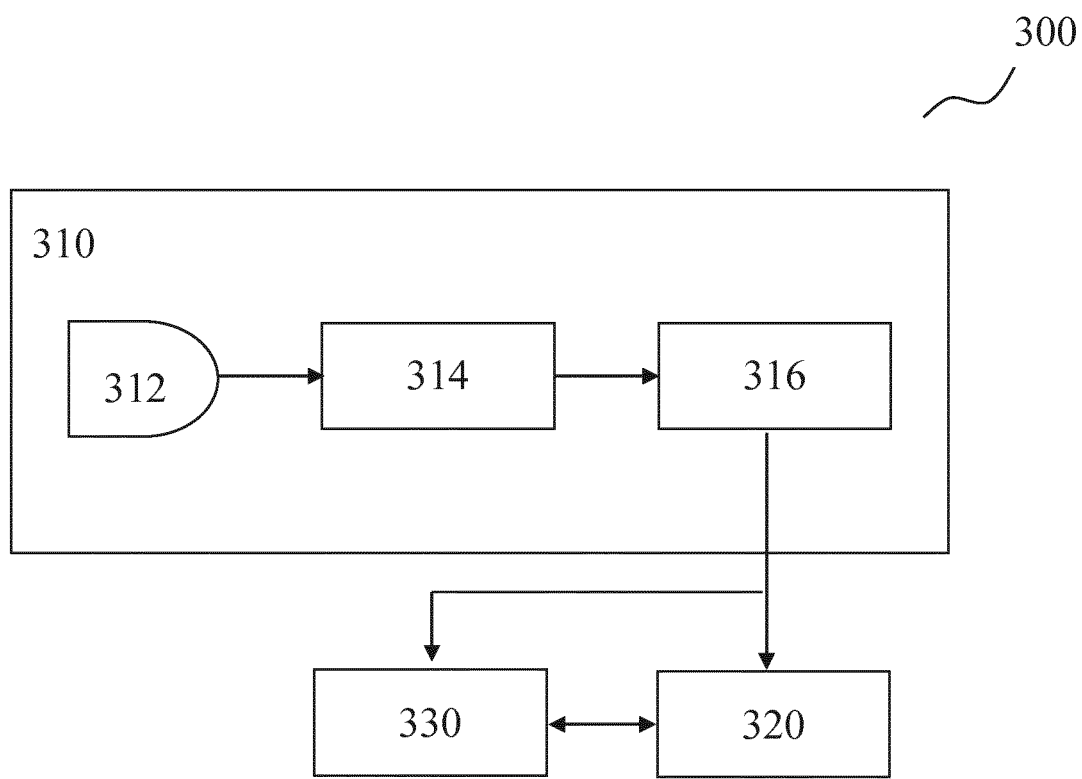
FIG. 3 illustrates an ultrasound system in accordance with an embodiment of the present invention.

FIG. 3 illustrates an ultrasound system in accordance with an embodiment of the present invention. The ultrasound system 300 can be a stand-alone ultrasound diagnostic imaging system which can be either fixedly mounted or equipped with wheels to enable movement. The ultrasound system 300 can be a compatible, portable device. The ultrasound system 300 can comprise an ultrasound probe connectable, for example via a USB interface, to any suitable portable device. The portal device can be a laptop, a tablet, a smart phone or the like.

The ultrasound system 300 comprises an ultrasound data acquisition unit 310 capable of acquiring ultrasound data frames. The acquisition unit 310 may comprise an ultrasound transducer array 312, a beamformer 314 and a signal processor 316. The ultrasound transducer array 312 can comprise piezoelectric transducer elements formed of materials such as PZT or PVDF. The ultrasound transducer can alternatively be a CMUT transducer. The ultrasound transducer array 312 can comprise a one- or two-dimensional array of transducer elements capable of scanning in a 2D plane or in three dimensions for 3D imaging. The ultrasound transducer array 312 can be a sector, linear, curved or matrixed ultrasound transducer. The ultrasonic transducer array 312 is configured to transmit ultrasonic energy and receive echoes returned in response to this transmission. A beamformer 314 can be configured to beamform the echo signals to produce coherent echo signals, such as ultrasound raw radio frequency data. The beamformed signals can be coupled to a signal processor 316. The signal processor 316 can process the received echo signals in various ways, such as bandpass filtering, decimation, I and Q component separation, and harmonic signal separation. The signal processor 316 can derive various ultrasound data, such as ultrasound radio frequency (RF) data, B-mode data, Doppler data, from the received ultrasound echo signals. For example, it may employ detection of an amplitude of the received ultrasound signal for the imaging of structures in the body such as the tissue of organs and vessels in the body. B mode images of structures of the body may be formed in either the harmonic image mode or the fundamental image mode or a combination of both as described in U.S. Pat. No. 6,283,919 (Roundhill et al.) and U.S. Pat. No. 6,458,083 (Jago et al.) The signal processor 316 can further arrange the echo signals in the spatial relationship in which they were received to form an ultrasound data frame. Ultrasound data frames acquired at different timepoints can form a temporal sequence of ultrasound data frames. The beamformer 314 and the signal processor 316 are illustrated as two units, but the person skilled in the art would appreciate that they are logic or functional units, and they can be implemented in a single unit or each of them can be implemented by more than one separate units. A so-called ultrasound probe, to be held by the clinicians during the examination, comprises at least the ultrasound transducer array 310, and can, optionally, comprise part or all of the functions of the ultrasound acquisition unit 310.

In accordance with an embodiment of the invention, the ultrasound acquisition unit 310 is configured to acquire, via the ultrasound transducer array 312, a temporal sequence of ultrasound data frames of a first region of interest including a pleural interface of a lung. Either a longitudinal scan 110 or an oblique scan 120 or both can be performed by the clinician to acquire the ultrasound data.

The ultrasound system 300 further comprises a data processor 320 for processing the temporal sequence of ultrasound data frames. The data processor 320 is coupled to the ultrasound acquisition unit 310. Additionally, the data processor 320 may be further coupled to a storage device of another apparatus, such as a hospital information system, and configured to retrieve the temporal sequence of ultrasound data frames from the storage device. The data processor 320 is configured to identify, for each of the ultrasound data frames, a sub-region of the scanned region of the ultrasound data frame, wherein the sub-region comprises at least part of the pleural interface. The data processor 320 is further configured to extract data of the sub-regions from the at least two ultrasound data frames, and to derive a parametric map for the sub-region on the basis of the extracted data. The parametric values of the parametric map indicate tissue motion over the at least two ultrasound frames.

The ultrasound system 300 further comprises a user interface 330 coupled to the data processor 320. The user interface 330 is configured to visualize the likelihood of lung sliding on the basis of the derived parametric map. The user interface 330 may be further configured to receive one or more user inputs.

Details of the derivation of the parametric map, the visualization of the likelihood of lung sliding, as well as the one or more user inputs will be described below with reference to FIG. 4 and FIG. 5.

Figure 4:
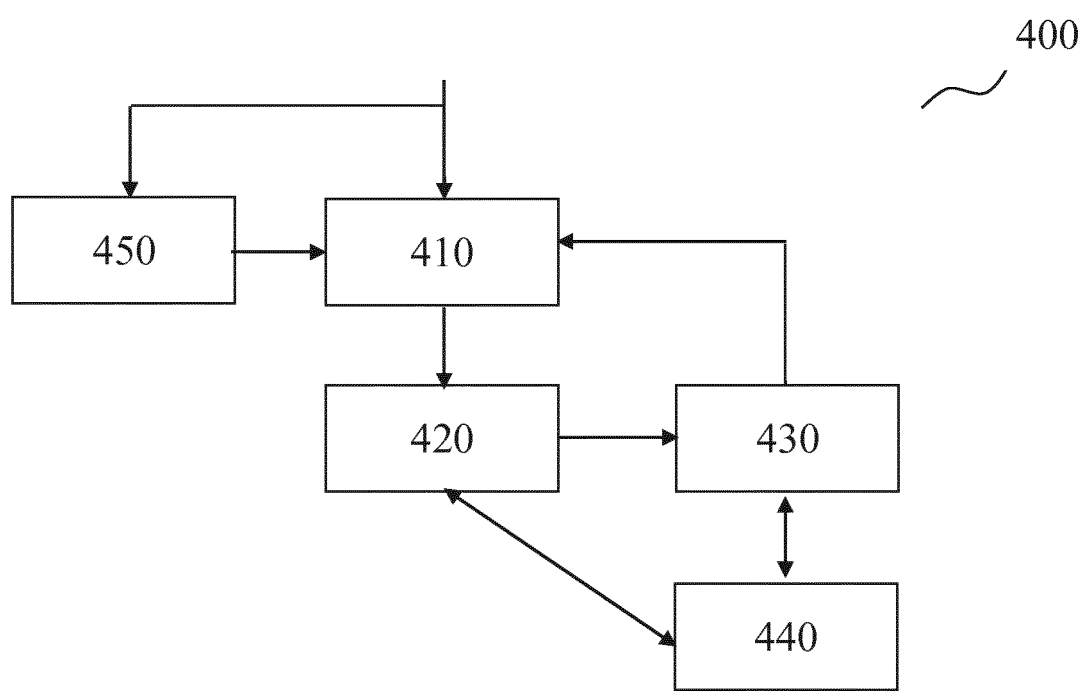
FIG. 4 illustrates an apparatus for detecting lung sliding in accordance with an embodiment of the present invention.

FIG. 4 illustrates an apparatus 400 for detecting lung sliding in accordance with an embodiment of the present invention. FIG. 5 illustrates a method 500 of detecting lung sliding in accordance with an embodiment of the present invention. The person skilled in the art would appreciate that the components in FIG. 4 and the steps in FIG. 5 are not intended to restrict the present invention, but merely show a particular embodiment of the present invention, and some of them may be optionally omitted or modified in various embodiments.

The apparatus 400 is configured to detect lung sliding on the basis of ultrasound data comprising a temporal sequence of ultrasound data frames of a first region of interest, wherein the first region of interest includes a pleural interface of a lung. In some embodiments, the apparatus 400 can be part of an ultrasound system, such as the data processor 320 of the ultrasound system 300. In some other embodiments, the apparatus 400 can be connectable to one or more storage devices for temporally or permanently storing ultrasound data, which may be the storage device of an ultrasound system, an ultrasound probe, a PACS system or other hospital information system.

In step S510, the apparatus 400 is configured to retrieve a temporal sequence of ultrasound data frames of a first region of interest, wherein the first region of interest includes a pleural interface of a lung. The apparatus 400 can detect lung sliding for a real-time temporal sequence of ultrasound data frames, or it can detect lung sliding during the post-processing of a previously acquired temporal sequence of ultrasound data frames. Accordingly, the temporal sequence of ultrasound data frames can be sequentially retrieved in a real-time data stream, such as frame by frame, or it can be retrieved at one time. The ultrasound data frame can be a B mode data frame, which is the most widely used ultrasound modality. The ultrasound data frame can be another ultrasound data frame as well, such as an ultrasound radio frequency data frame, or any other suitable ultrasound data frame derived from the ultrasound radio frequency data frame.

The apparatus 400 comprises a sub-region identifier 410. The sub-region identifier is configured to identify, in step S520, for each of the ultrasound data frames, a sub-region of the scanned region of the ultrasound data frame, wherein the sub-region comprises at least part of the pleural interface. The sub-region is preferably of the same size across the ultrasound data frames so as to simplify the calculation of the parametric map. In one embodiment, the identified sub-region is the same among a plurality of ultrasound data frames, or among all the ultrasound data frames, of the temporal sequence. This is under the assumption that although the location of the pleural interface may change across the ultrasound data frames, such change is limited in the same scan of a certain lung, and so the location of the sub-region need not be updated every frame, provided that the size of the sub-region is sufficiently large to tolerate such change. For example, the sub-region is first identified in one of the plurality of ultrasound data frames, such as the first ultrasound data frame, and then the same sub-region is applied to all the other ultrasound frames of the plurality of ultrasound data frames. In another embodiment, the identified sub-region may be individually identified for each of the ultrasound data frames, in which case the size of the sub-region can be set smaller at the cost of more complexity.

For a certain ultrasound data frame, the sub-region can be identified in different ways in various embodiments.

In some embodiments, the sub-region is identified on the basis of one or more predetermined parameters. The one or more predetermined parameters can be set by default, by user selection, or it can be derived on the basis of other parameters. In an example, the one or more predetermined parameters comprise a predetermined depth range, and the sub-region is identified as part of the scanned region within the predetermined depth range. Based on the observation that the pleural interface is typically about 1.5-5 cm down from the top (i.e. skin surface) of the scanned region, the predetermined depth range can be set to 0-6 or 1-6 cm for example. Based on the observation that the depth of the pleural interface increases with the BMI (body mass index) of the subject, the predetermined depth range can be adjusted on the basis of the BMI of the subject. Based on the observation that the pleural interface is approximately 0.5 cm below the ribs, the predetermined depth range can be set on the basis of the depth of the rib(s). In an example, the one or more predetermined parameters may further comprise a lateral position of one or more ribs present in the scanned region, e.g. in the case of a longitudinal scan, and the sub-region can be identified as part of the scanned region within a predetermined lateral range so as to exclude rib-shadow.

In some other embodiments, the apparatus 400 further comprises a pleural line detector 450. The pleural line detector 450 is configured to detect, in step S560, a pleural line in at least one of the ultrasound data frames, and the sub-region identifier 410 is configured to identify, in step 520, the sub-region for each of the ultrasound data frames on the basis of the detected pleural line. Once the pleural line is automatically detected in an ultrasound data frame, the sub-region in that ultrasound image can be identified as surrounding the detected pleural line. For example, along the depth direction, the top and bottom edges of the identified sub-region are identified respectively as extending above and below the detected pleural line by a predetermined depth value, such as 0.25 cm or 0.5 cm. In other words, the identified sub-region can be a fixed-size band or strip following the detected pleural line. The predetermined depth value can be set or dynamically changed via a user interface, and/or it can be configured by a configure file. For example, along the lateral direction, the left and right ends of an identified sub-region are identified as being the same as the two ends of the detected pleural line. The pleural line appears to be substantially horizontal, but normally it is not a straight line, and thus the corresponding sub-region appears as a kind of strip following the detected pleural line. In the embodiment illustrated in FIGS. 6A-6C, the sub-region 630 is identified as a strip surrounding the detected pleural line 640 by 0.25 cm on each side along the depth direction. The skilled person would understand that the lateral direction is a direction perpendicular to the depth direction (which is the transceiver direction of the ultrasound signal, and which is also called range direction), and in case of three dimensional imaging, the lateral direction can be the elevation direction, or the azimuth direction, or any direction in the plane perpendicular to the depth direction. In another example, the sub-region can have a regular shape, such as a rectangular box surrounding or encompassing the detected pleural line.

Figure 8:
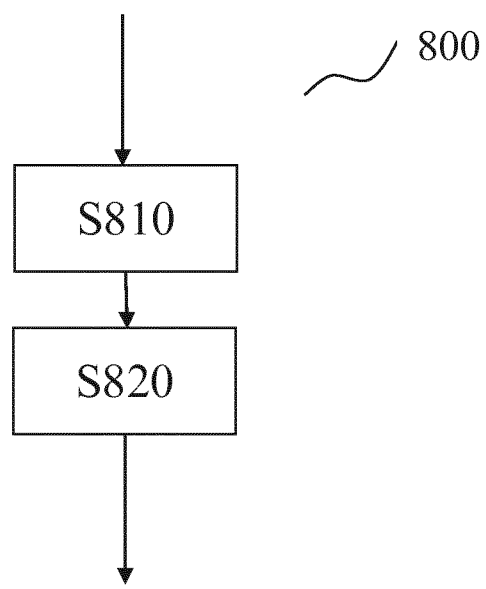
FIG. 8 illustrates a method of detecting a pleural line in accordance with an embodiment of the present invention.

The automatic detection of the pleural line can be implemented by means of any suitable existing and future-developed detection algorithm. FIG. 8 illustrates a method 800 of detecting a pleural line in accordance with an embodiment of the present invention. The pleural line detector 450 is configured to estimate, in step S810, a depth of the pleural interface, and to detect, in step S820, a pleural line in the at least one ultrasound data frame of the temporal sequence on the basis of the estimated depth.

In one embodiment, in step S810, the depth of the pleural interface is estimated on the basis of multiple ultrasound data frames of the temporal sequence. The number of multiple ultrasound data frames can be experimentally selected. In one embodiment, the number of multiple ultrasound data frames is 16, although more or fewer ultrasound data frames could be used, as desired. In particular, the step S810 of estimating the depth of the pleural interface comprises: a sub-step of deriving, for each of one or more predetermined lateral positions, an intensity profile representing an intensity value as a function of depth, each intensity value indicating an averaged ultrasound data value at the corresponding depth over multiple ultrasound data frames of the temporal sequence, on the basis of the multiple ultrasound data frames of the temporal sequence. The step S810 further comprises a sub-step of estimating the depth of the pleural interface on the basis of the derived intensity profile(s). The one or more predetermined lateral positions may comprise the center lateral position. For example, in case a scanned region has a width of 4 cm, one predetermined lateral position is at 2 cm. Additionally or alternatively, the one or more predetermined lateral positions may comprise two lateral positions a predetermined distance away from the center lateral position. For example, in case a scanned region has a width of 4 cm, the predetermined lateral positions may further comprise lateral positions at 1 cm and 2 cm. The intensity value at a certain depth can be a sum, average, or weighted average of all ultrasound data values at that depth in the multiple ultrasound data frames.

Figure 9:
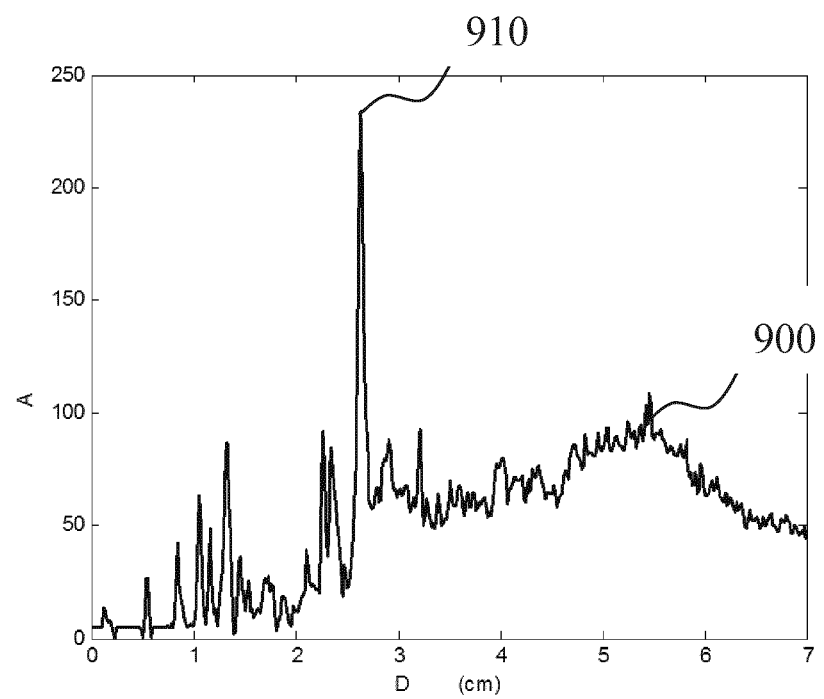
FIG. 9 illustrates an intensity profile representing an intensity value averaged over multiple ultrasound data frames as a function of depth values derived in accordance with an embodiment of the present invention.

FIG. 9 illustrates an intensity profile 900 representing an intensity value averaged over multiple B-mode ultrasound data frames as a function of depth values derived in accordance with an embodiment of the present invention. The intensity profile 900 is derived on the basis of the ultrasound values at the center lateral position over 16 ultrasound data frames. The x-axis represents the depth values D, in unit of cm, and the y-axis represents the intensity value A averaged over the multiple ultrasound data frames. Referring to FIG. 9, the highest peak 910 appears at approximately 2.63 cm. Accordingly, the point at the depth of 2.63 cm and the center lateral position can be used as the initial search points (?) in step S820. In some embodiments, additional prior knowledge may be used to estimate the depth of the pleural interface, especially for cases where there are multiple peaks in the intensity profile. For example, the rib also appears as a bright horizontal line. The prior knowledge includes, but is not limited to: the pleural line depth is equal to the chest wall thickness, which is typically around 2 cm from the surface for adults, the averaged distance between the pleural line and the rib is around 0.5 cm for adults, and the chest wall thickness (CWT) is predictable from the body mass index, and there is a lower intensity value below the rib than below the pleural line due to the rib-shadowing, etc.

In another embodiment, in step S810, the depth of the pleural interface is estimated on the basis of an ultrasound data frame of a second region of interest including a pleural interface of the lung and at least one rib. Such ultrasound data frame is acquired in a longitudinal scan, and the second region of interest is a transverse view of the lung. In case the temporal sequence of ultrasound data frames is acquired in a longitudinal scan, the second region of interest can be the same as the first region of interest and thus the ultrasound data frame used to estimate the depth of the pleural line can be one ultrasound data frame of the temporal sequence of the first region of interest. In case the temporal sequence of ultrasound data frames is acquired in an oblique scan, the second region of interest is different from the first region of interest and the ultrasound data frame of the second region is acquired in an additional longitudinal scan. In this case, the clinician may first perform a longitudinal scan to acquire one ultrasound frame for estimating the depth of the pleural interface, and then perform an oblique scan to acquire a temporal sequence of ultrasound frames for detecting lung sliding. In particular, the step S810 of estimating the depth of the pleural interface comprises: estimating the depth of the at least one rib on the basis of the ultrasound data frame of the second region, and then estimating the depth of the pleural interface on the basis of the estimated depth of the at least one rib and a predetermined value. For instance, the depth of the pleural interface is estimated as being 0.5 cm below the estimated depth of the at least one rib.

Figure 10:
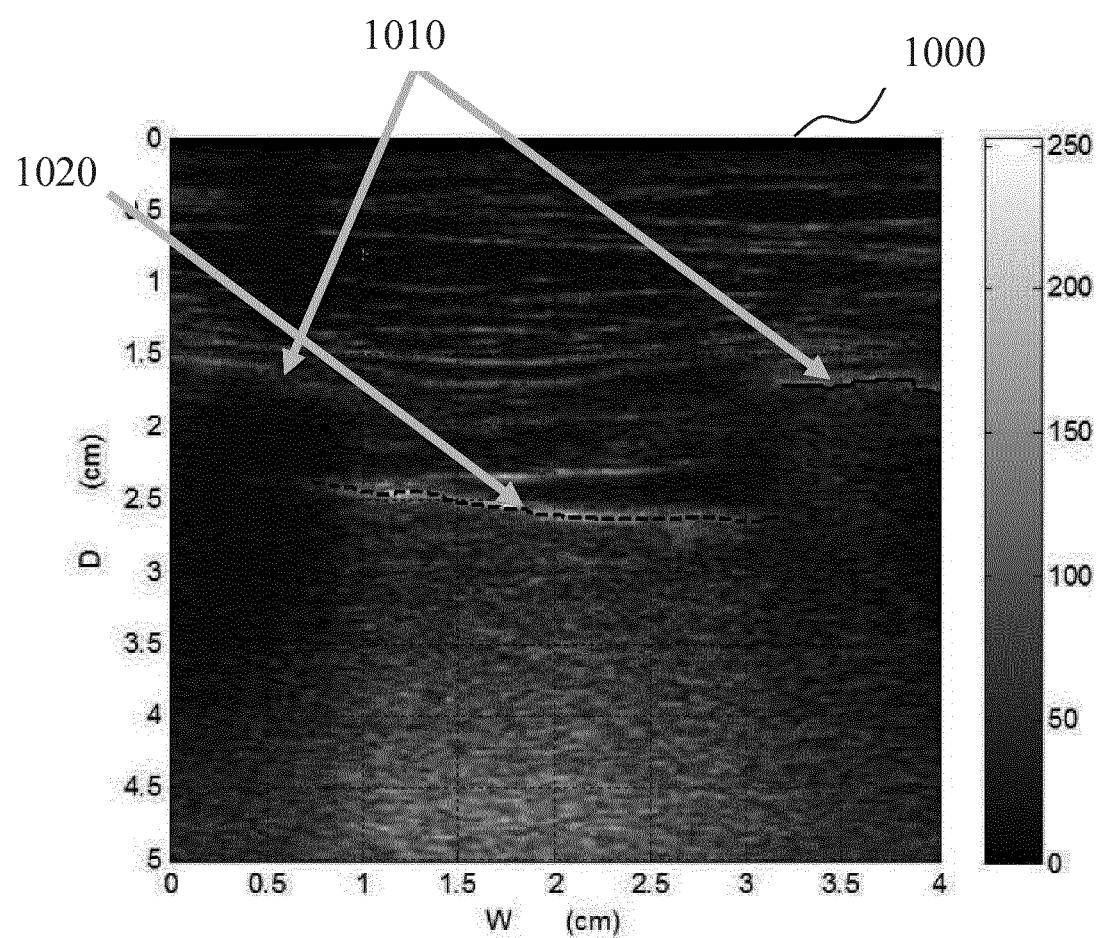
FIG. 10 illustrates, in an ultrasound B-mode image, a pleural line detected in accordance with an embodiment of the present invention.

FIG. 10 illustrates, in an ultrasound B-mode image 1000, a pleural line detected on the basis of detected rib positions in accordance with an embodiment of the present invention. Referring to FIG. 10, the x-axis represents the width of the scanned region, the y-axis represents the depth of the scanned region, and the gray value represents the image value. Two ribs 1010 are detected as being located at a depth of around 1.65 cm and in the width range of 0 to 0.5 cm and 3.15 to 4 cm, and the location of the pleural line is estimated as being at a depth of 2.4 to 2.65 cm.

Once the estimated depth of the pleural interface is available, the pleural line in the at least one ultrasound data frame can be detected by any suitable detection algorithms. In particular, the estimated depth of the pleural interface is used as initial search point, and the pleural line is searched at locations surrounding the estimated depth of the pleural interface, which reduces the complexity and increases the reliability. For example, starting from the initial search point, the detection algorithm searches for neighboring pleural line points and continues to grow the detected pleural line along the lateral directions.

In one embodiment, the pleural line can be detected in each ultrasound data frame by using the depth of the pleural interface estimated in step S810 as initial search point. In another embodiment, once the pleural line is detected in one ultrasound data frame, the pleural line in an ultrasound data frame adjacent to that ultrasound data frame is detected on the basis of the detected pleural line. This is under the assumption that there is less change in the location of the pleural line between adjacent ultrasound frames.

Figure 5:
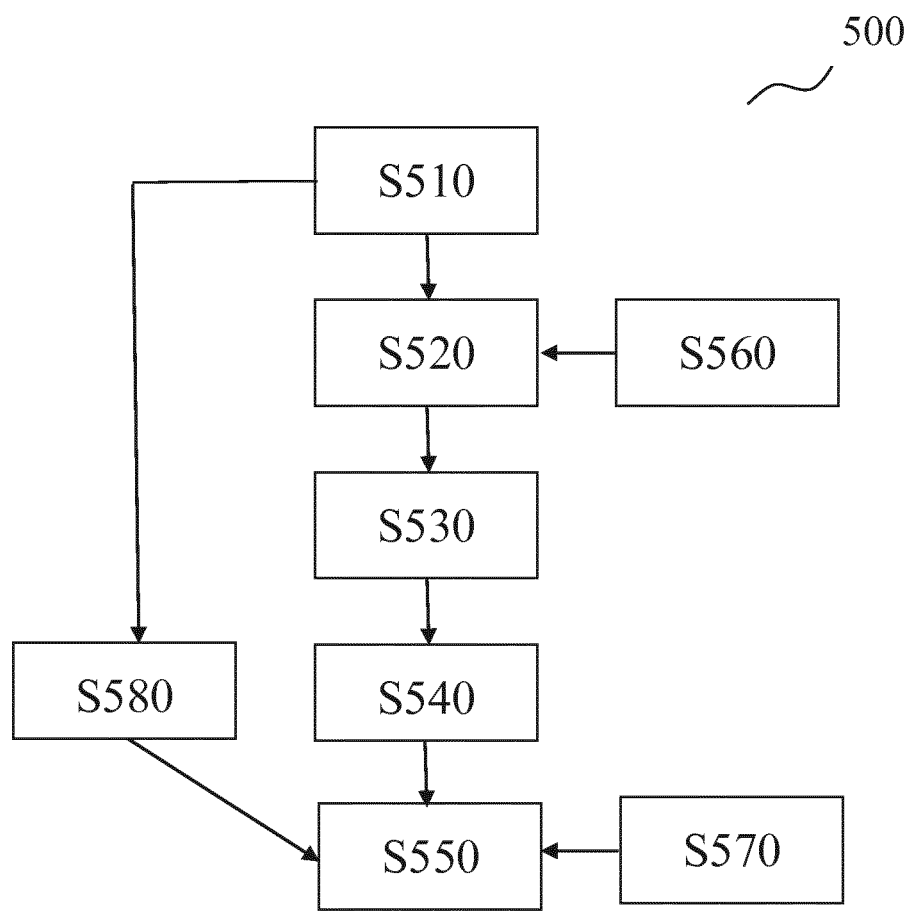
FIG. 5 illustrates a method of detecting lung sliding in accordance with an embodiment of the present invention.

Referring to FIG. 4 and FIG. 5, the apparatus 400 further comprises a lung sliding detector 420. The lung sliding detector 420 is configured to extract, in step S530, data of the sub-regions from at least two ultrasound data frames of the temporal sequence, and to derive, in step S540, a parametric map for the sub-region on the basis of the at least two ultrasound data frames, wherein parametric values of the parametric map indicate a degree of tissue motion over the at least two ultrasound frames. The number of the at least two ultrasound frames can be experimentally selected. For example, the number of the at least two ultrasound frames is 16. The parametric map can be derived every frame or every predetermined number of frames. Assuming that the number of the at least two ultrasound frames is N, in case the number of the parametric map is updated every frame, the parametric map is derived from the current frame and the previous N−1 frames.

In some embodiments, the parametric value can be derived by estimating the motion vector by performing block correlation or normalized cross correlation, or by calculating optical flow vectors. Due to tissue motion, the same tissue point may appear at different pixel locations in different ultrasound data frames. The distance over which the same tissue point moves can be used to represent the degree of the tissue motion. The aforementioned algorithms intend to determine the motion of individual tissue points so as to assess the degree of the tissue motion.

In some other embodiments, it is proposed to measure a single-pixel intensity change over time caused by the tissue motion, rather than estimating the motion vector of the tissue motion. In particular, the parametric value for a pixel location in the scanned region indicates, and for example is proportional to, an amount of change in ultrasound data values of the pixel location over the at least two ultrasound data frames caused by the tissue motion. Such single-pixel intensity change can be derived using various methods, including but not limited to pixel-by-pixel correlation, FFT algorithm, differentiation etc.

Referring to FIG. 4 and FIG. 5, the apparatus 400 further comprises a user interface 430. The user interface 430 is configured to visualize, in step S550, the likelihood of lung sliding on the basis of the derived parametric map. The user interface 430 can be further configured to optionally visualize the detected pleural line. In some embodiments, the detected pleural line is displayed as a line, which delineates the detected pleural line, overlaid on an image of at least the sub-region. The line can be in any suitable format, such as solid, dashed, or colored. For example, the line can be colored in white, dark, red or a color selected by the user. The user interface 430 can be further configured to optionally visualize the identified sub-region. In some embodiments, the identified sub-region is displayed as a box which delineates the identified sub-region.

The visualization of the likelihood of lung sliding can be implemented in various ways.

In an embodiment, the user interface 430 is configured to visualize the likelihood of lung sliding by presenting the derived parametric map in the form of a parametric image, overlaid with an image of at least the sub-region. The image of at least the sub-region can be generated on the basis of at least one of the ultrasound data frames of the sequence. The parametric image can be color coded or gray-scale coded. The image of at least the sub-region can be an ultrasound B-mode image of the scanned region. The image of at least the sub-region can also be an ultrasound B-mode image of part of the scanned region which comprises the sub-region. The overlaid image of at least the sub-region can be generated on the basis of one of the at least two ultrasound data frames used to derive the parametric map, such as the latest frame of the at least two ultrasound data frames.

Figure 6A:
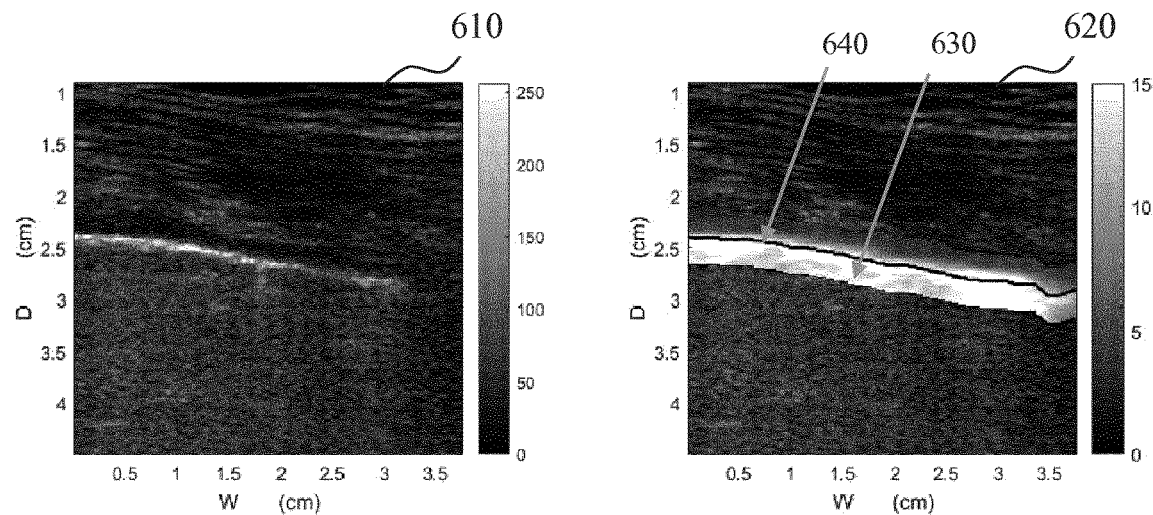
Figure 6B:
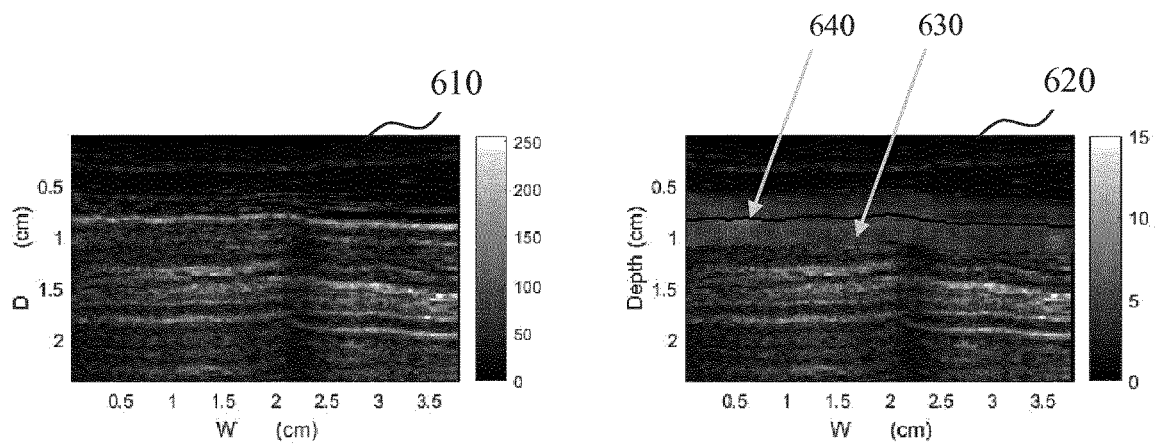
Figure 6C:
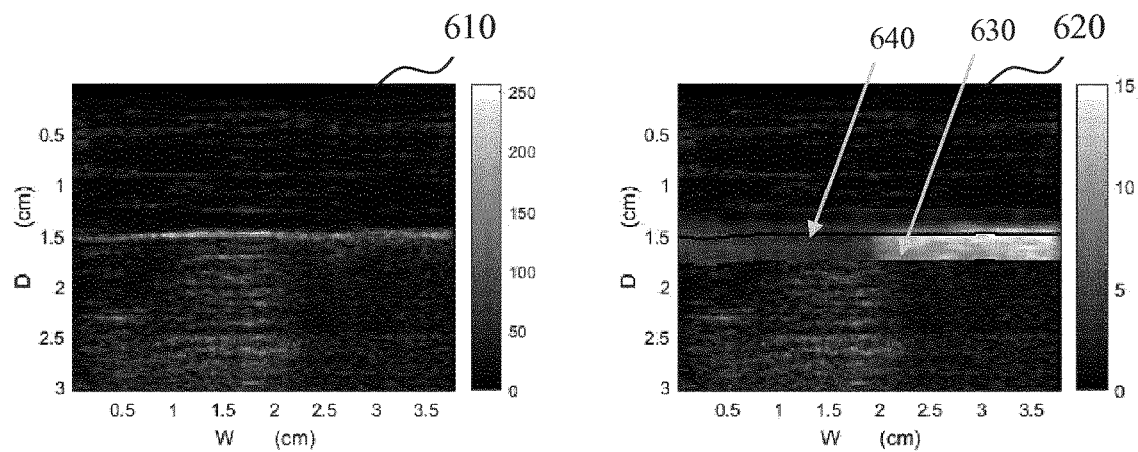

FIGS. 6A-6C each illustrate an ultrasound B-mode image 610 and a combined image 620 of the ultrasound B-mode image 610 overlaid with a parametric image 630 in accordance with an embodiment of the present invention, wherein FIG. 6A illustrates a case where lung sliding is present, FIG. 6B illustrates a case where lung sliding is absent, and FIG. 6C illustrates a case where lung sliding is partially present. In each of FIGS. 6A-6C, the x-axis represents the width of the scanned region, the y-axis represents the depth of the scanned region, and the gray value represents the image value of the B-mode image or the parametric image, wherein a higher parametric value is represented by a brighter gray value. Alternatively, the B-mode image 610 can be gray-scale coded and the parametric image 630 can be color-coded. Furthermore, the detected pleural line 640 is delineated as a black solid line.

Referring to FIG. 6A, the sub-region, especially the part of the sub-region below the detected pleural line, appears to be relatively brighter, which corresponds to higher parametric values. Since higher parametric values indicate a higher degree of tissue motion, this also indicates the presence of lung sliding. Referring to FIG. 6B, the sub-region appears to be relatively dark, which corresponds to a lower parametric value, and thus indicates the absence of lung sliding. Referring to FIG. 6C, the parametric image of the sub-region changes from dark to bright at a width of about 2 cm, which indicates that lung sliding is absent in the width range of 0 to 2 cm, lung sliding is present in the width range of 2 to 4 cm, and a lung point is present at the width of about 2 cm.

In another embodiment, the user interface 430 is configured to visualize the likelihood of lung sliding by presenting a sliding profile in the format of a strip, overlaid with or next to an image of at least the sub-region. In particular, the lung sliding detector 420 is further configured to derive, on the basis of the parametric map, the sliding profile. The sliding profile represents sliding values as a function of lateral positions of the pleural interface, wherein each sliding value for a lateral position indicates the likelihood of lung sliding at the lateral position; and the user interface 430 is further configured to present the derived sliding profile. In an embodiment, the sliding value for a particular lateral position is derived as indication of the averaged parametric value for that particular lateral position over the depth direction. For example, the sliding value can be a sum, average, or weighted average of the parametric values at all depths at that particular lateral position.

FIGS. 7A-7C each illustrate a combined image of an ultrasound B-mode image 710 and a horizontal strip 720 for indicating the likelihood of lung sliding in accordance with an embodiment of the present invention, wherein FIG. 7A illustrates a case where lung sliding is present, FIG. 7B illustrates a case where lung sliding is absent, and FIG. 7C illustrates a case where lung sliding is partially present.

Referring to the B-mode image 710 illustrated in each of FIGS. 7A-7C, the x-axis represents the width of the scanned region, the y-axis represents the depth of the scanned region, and the gray value represents the image value of the B-mode image. Referring to the horizontal strip 720, the sliding values are gray-scale coded, wherein a higher sliding value is coded as a brighter gray value. The horizontal strip represents sliding values as a function of the lateral positions and is aligned with the B-mode image in lateral positions, namely the widths in FIGS. 7A-7C. Instead of a gray-scale, the horizontal strip 720 can be color-coded.

Referring to FIG. 7A, the horizontal strip 720 is dominant due to the brighter values, which corresponds to higher sliding values. Since higher sliding values indicate a higher degree of tissue motion, this also indicates the presence of lung sliding. Referring to FIG. 7B, the horizontal strip 720 appears to be dark at all lateral positions, and thus indicates the absence of lung sliding. Referring to FIG. 7C, the horizontal strip changes from dark to bright at a width of about 2 cm, which indicates that lung sliding is absent in the width range of 0 to 2 cm, lung sliding is present in the width range of 2 to 4 cm, and a lung point is present at the width of about 2 cm.

In another embodiment, the user interface 430 is configured to visualize the likelihood of lung sliding by presenting a value indicating the percentage of the presence of lung sliding. Theoretically, the percentage is 100% in the case of full presence of lung sliding in the scanned region, the percentage is 0% in the case of no lung sliding in the scanned region, and the percentage is between 0%-100% in the case of partial lung sliding, where a lung point may be present. In particular, the lung sliding detector 420 is configured to derive a value for indicating the percentage of the presence of lung sliding along the lateral direction on the basis of the parametric map or the sliding profile. In an embodiment, the value is derived by comparing the sliding values with a predetermined threshold. For example, the value is derived as being equal to the percentage of sliding values which are greater than the predetermined threshold.

The user interface 430 may be further configured to receive, in step S570, one or more user inputs.

In an embodiment, the user interface 430 is configured to receive a user input for indicating a modification of the grayscale-coding or color-coding scheme used to visualize the parametric map or the sliding profile, and to modify the visualization on the basis of the received user input.

In another embodiment, the user interface 430 is configured to receive a user input for indicating a modification to the identified sub-region, and the sub-region identifier 410 is configured to modify the identified sub-region on the basis of the received user input. In an example, the user interface 430 is a touchscreen, and the user input comprises a finger operation on the corresponding region of the touchscreen where the parametric map or the identified sub-region is presented.

In another embodiment, the user interface 430 is configured to receive a user input for starting the method 500 of detecting lung sliding. A button or menu can be provided on the user interface 430 and the button or menu will initiate an automatic lung ultrasound feature extraction app, such as the method 500 of detecting lung sliding.

In another embodiment, the user interface 430 is configured to receive a user input for setting and/or changing one or more parameters used in the method 500. Such setting or changing can be performed prior to performing the method 500, or it can be performed on the fly during performing the method 500. In some embodiments, the one or more parameters comprise parameters used in identifying the sub-region such as the predetermined depth value, or parameters used in detecting the pleural line such as the number of multiple ultrasound frames for estimating the depth of the pleural interface, or parameters used in determining background motion such as the predetermined threshold, or the like. In some embodiments, various user input means such as sliding bars, text input boxes, selectable lists or the like can be provided in the user interface 430 so as to receive one more user inputs.

Additionally or alternatively, the one or more parameters can be configured on the basis of a configuration file.

Further referring to FIG. 4 and FIG. 5, the apparatus 400 may further comprise a background motion detector 440 coupled to the lung sliding detector 420 and/or user interface 430. In step S580, the background motion detector 440 is configured to detect a degree of background motion and determine whether the degree of background motion exceeds a predetermined threshold. Then, the user interface 430 is configured to present the derived parametric map only if the degree of background motion does not exceed the predetermined threshold. Additionally or alternatively, the user interface 430 is configured to present an indicator for indicating the degree of background motion if the degree of background motion exceeds the predetermined threshold. Optionally, the lung sliding detector 420 can be configured to derive the parametric map only if the degree of background motion does not exceed the predetermined threshold. In an embodiment, the degree of background motion is determined on the basis of the derived parametric map. The background motion may be determined in other ways, such as by means of any motion detection algorithm or additional sensor equipped on the probe etc. Preferably, in accordance with an embodiment of the invention, the degree of background motion is quantified as an average of the parametric values above the pleural line.

Figure 11:
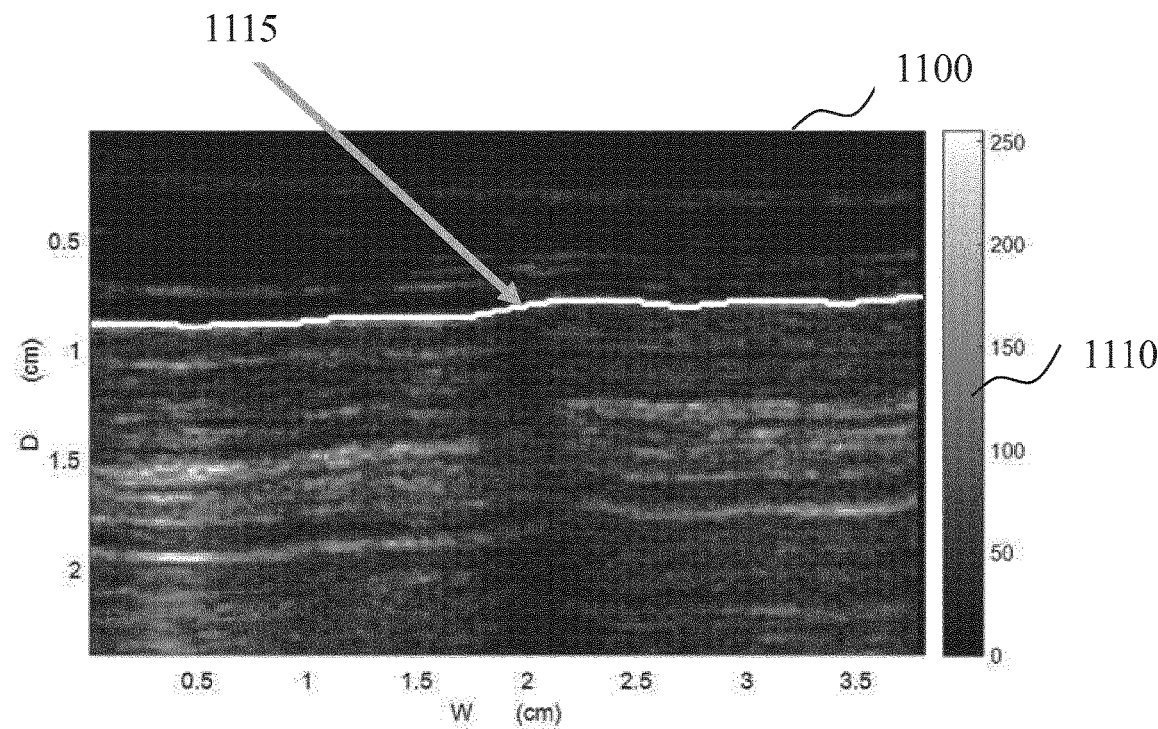
FIG. 11 illustrates an ultrasound B-mode image overlaid with a line for visualizing the detected pleural line in accordance with an embodiment of the present invention.

FIG. 11 illustrates an ultrasound B-mode image 1100 overlaid with a line 1115 for visualizing the detected pleural line in accordance with an embodiment of the present invention. In FIG. 11, the line 1115 delineates the detected pleural line, and is colored in white. Alternatively, the line 1115 can be colored in any suitable color. Optionally, the color of the line 1115 is selectable by the user. In FIG. 11, the bar 1110 represents the gray scale of the ultrasound B-mode image 1100. The bar 1110 is optionally presented by the user interface.

Figure 12:
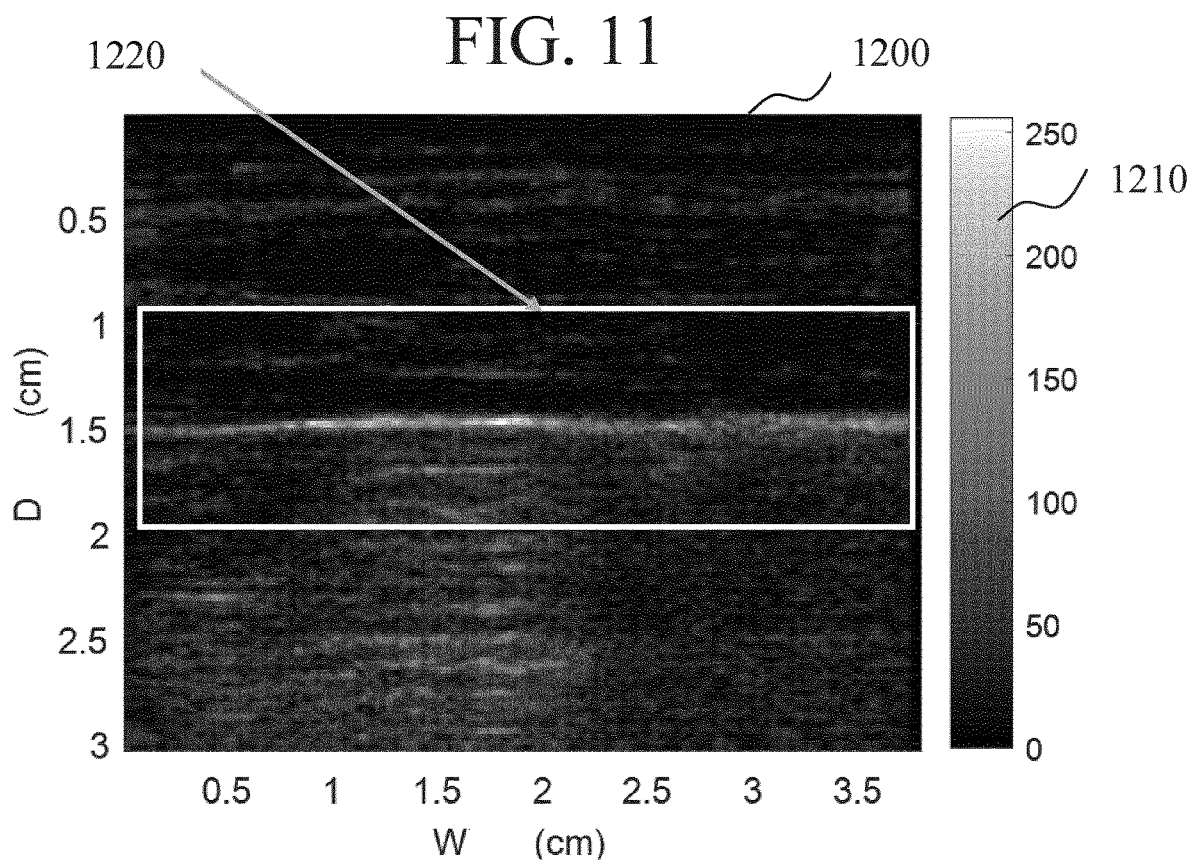
FIG. 12 illustrates an ultrasound B-mode image overlaid with a box for visualizing the identified sub-region in accordance with an embodiment of the present invention.

FIG. 12 illustrate an ultrasound B-mode image 1200 overlaid with a box 1220 for visualizing the identified sub-region in accordance with an embodiment of the present invention. The bar 1210 represents the gray scale of the ultrasound B-mode image 1200. The bar 1210 is optionally presented by the user interface. The rectangular box 1220 is used to indicate the identified sub-region. In case the identified sub-region itself is in a rectangular shape, the rectangular box 1220 delineates the identified sub-region. In case the identified sub-region is not rectangular shaped, the rectangular box 1220 can encompass the identified sub-region. In an example, the upper and bottom edges of the box 1220 correspond to the topmost point and the bottommost point of the identified sub-region, respectively. In another example, the upper edge of the box 1220 is set at around 0.5 cm, or any suitable predetermined value, above the highest point of the detected pleural line, and the bottom edge of the box 1220 is set at around 0.5 cm, or any suitable predetermined value, below the lowest point of the pleural line. The edges of the box 1220 can be presented in various forms. As illustrated in FIG. 12, the edges of the box 1220 are solid lines colored in white. Alternatively, the edges of the box 1220 can be colored in other colors such as red, or the edges of the box 1220 are in the form of dotted or dashed lines instead of a solid line.

Figure 13A:
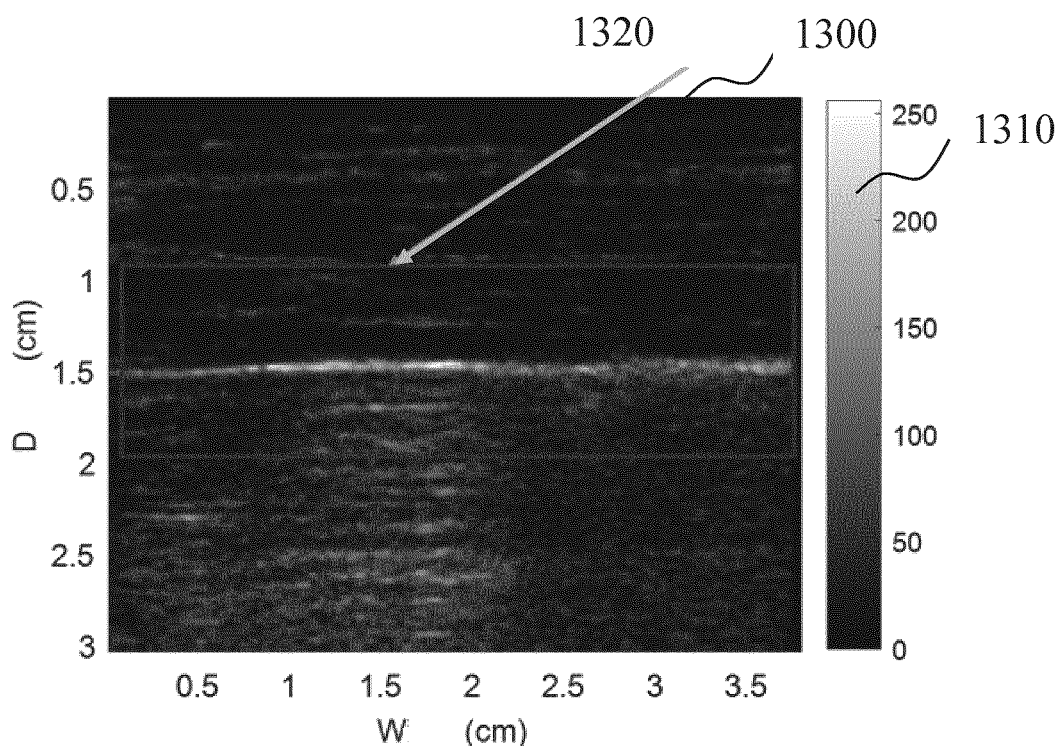
FIGS. 13A-13D each illustrate an ultrasound B-mode image and an indicator for indicating the degree of background motion if the degree of background motion exceeds the predetermined threshold in accordance with an embodiment of the present invention.
Figure 13B:
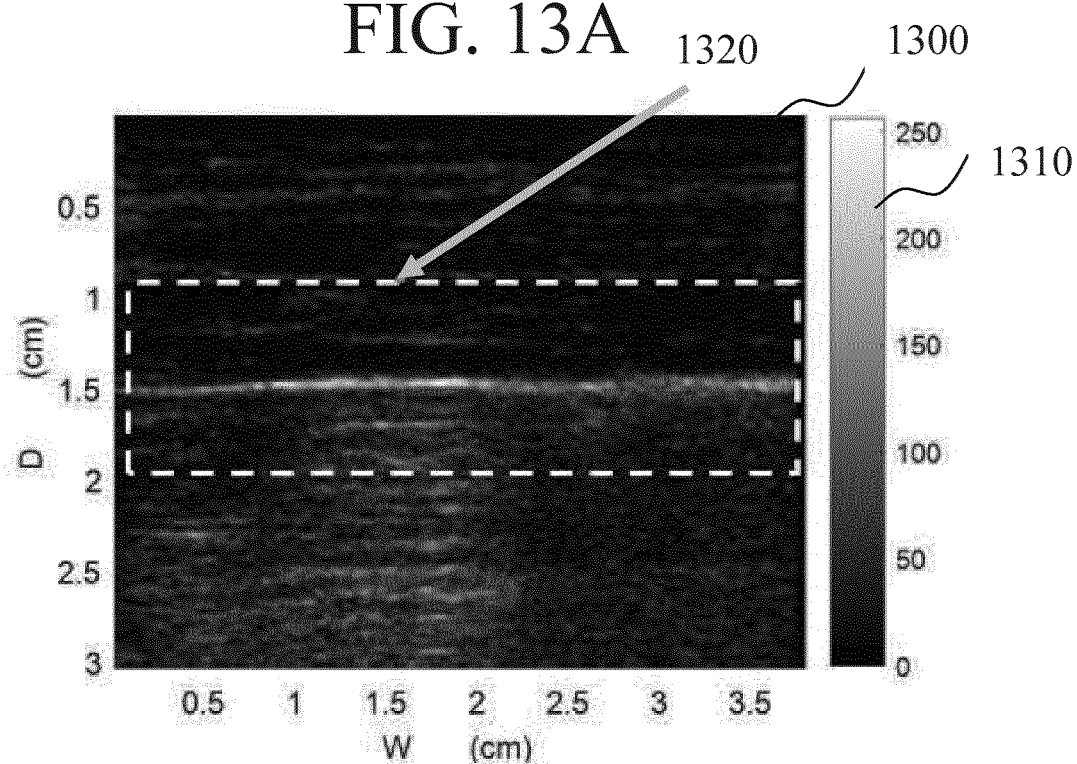
Figure 13C:
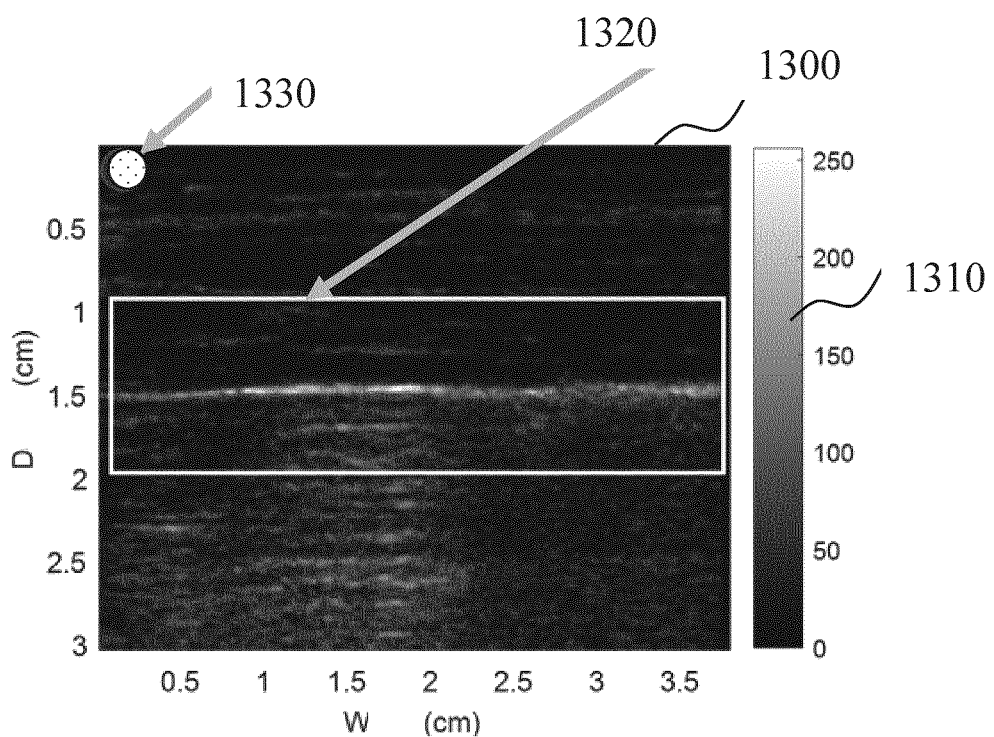
Figure 13D:
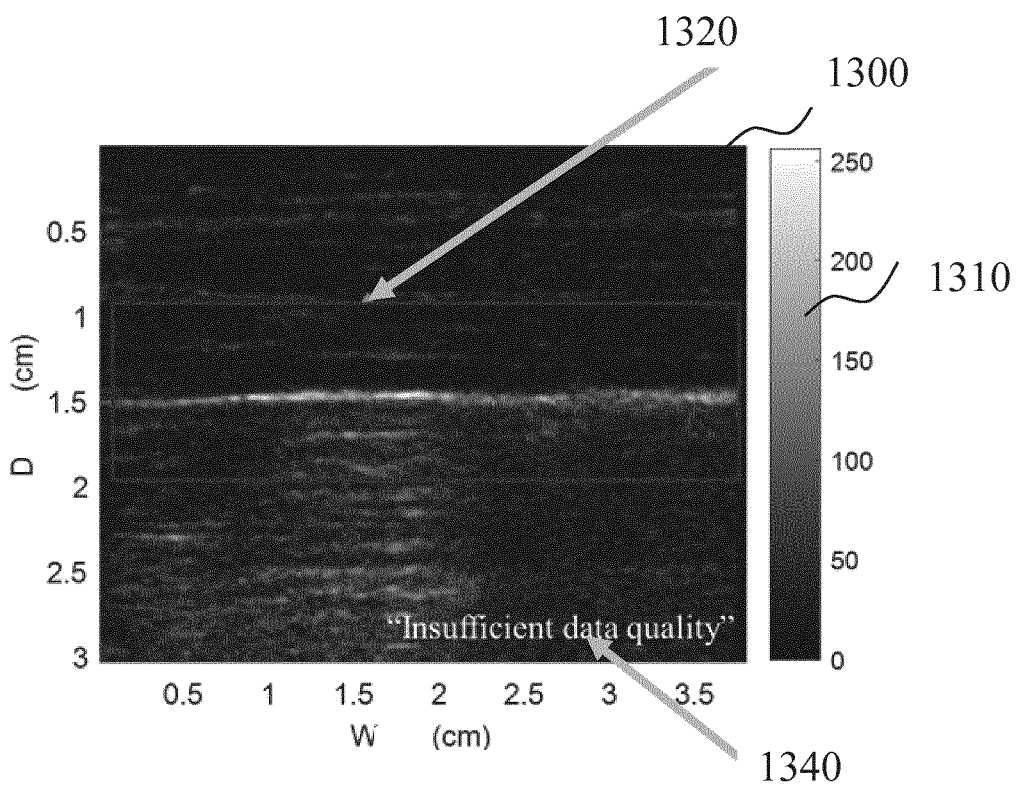

FIGS. 13A-13D each illustrate an ultrasound B-mode image 1300 and an indicator for indicating the degree of background motion if the degree of background motion exceeds the predetermined threshold in accordance with an embodiment of the present invention. In some embodiments, the indicator can be a color change or format change of the box 1320 for indicating the identified sub-region. As illustrated in FIG. 13A, the edges of the box 1320 are changed from a color to a different color, such as from white to red, to indicate a strong background motion. As illustrated in FIG. 13B, the edges of the box 1320 are changed from a solid line to a dashed or dotted line in color to indicate a strong background motion. Alternatively, the box 1320 can be set to flash if the detected background motion is strong, e.g. above a certain threshold. As illustrated in FIG. 13C, a flashing spot 1330 can be used as the indicator. For example, a flashing red spot 1330 indicates a strong background motion, and a solid green spot 1330 indicates no background motion. Alternatively or additionally, one or more text lines can be displayed at any suitable location to indicate a strong background motion. As illustrated in FIG. 13D, the text line 1340 "insufficient data quality" is displayed adjacent to the bottom side of the ultrasound B-mode image 1300.

Figure 14A:
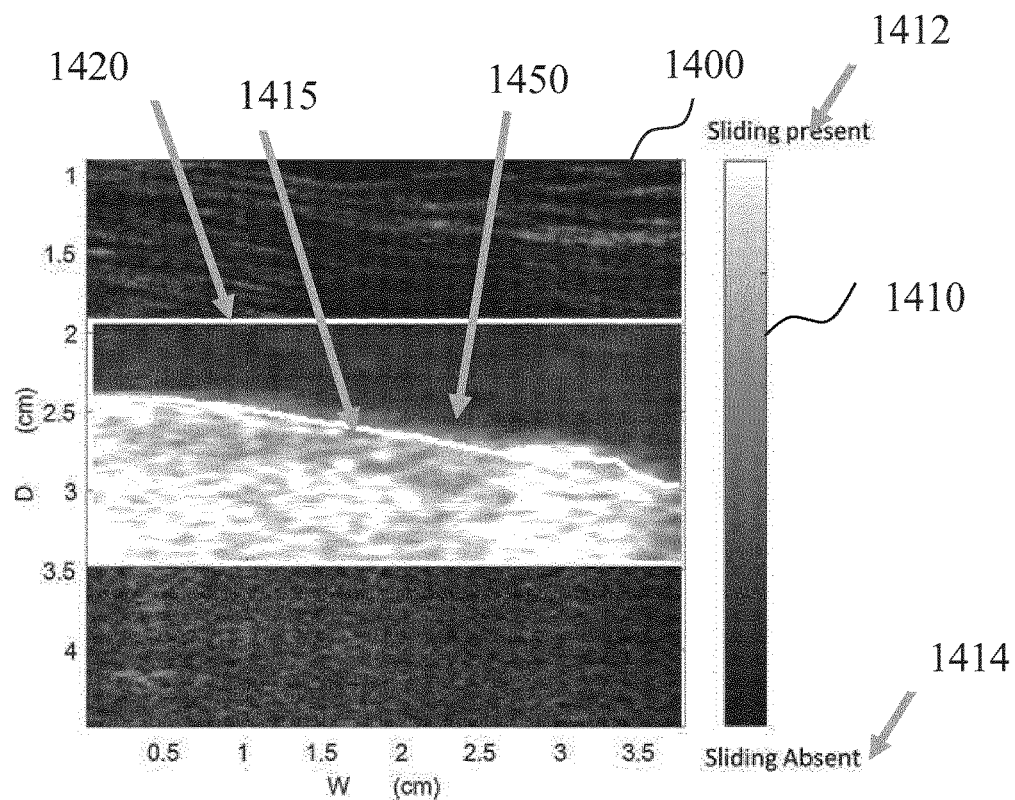
FIGS. 14A-14E each illustrate an ultrasound B-mode image overlaid with a parametric image.
Figure 14B:
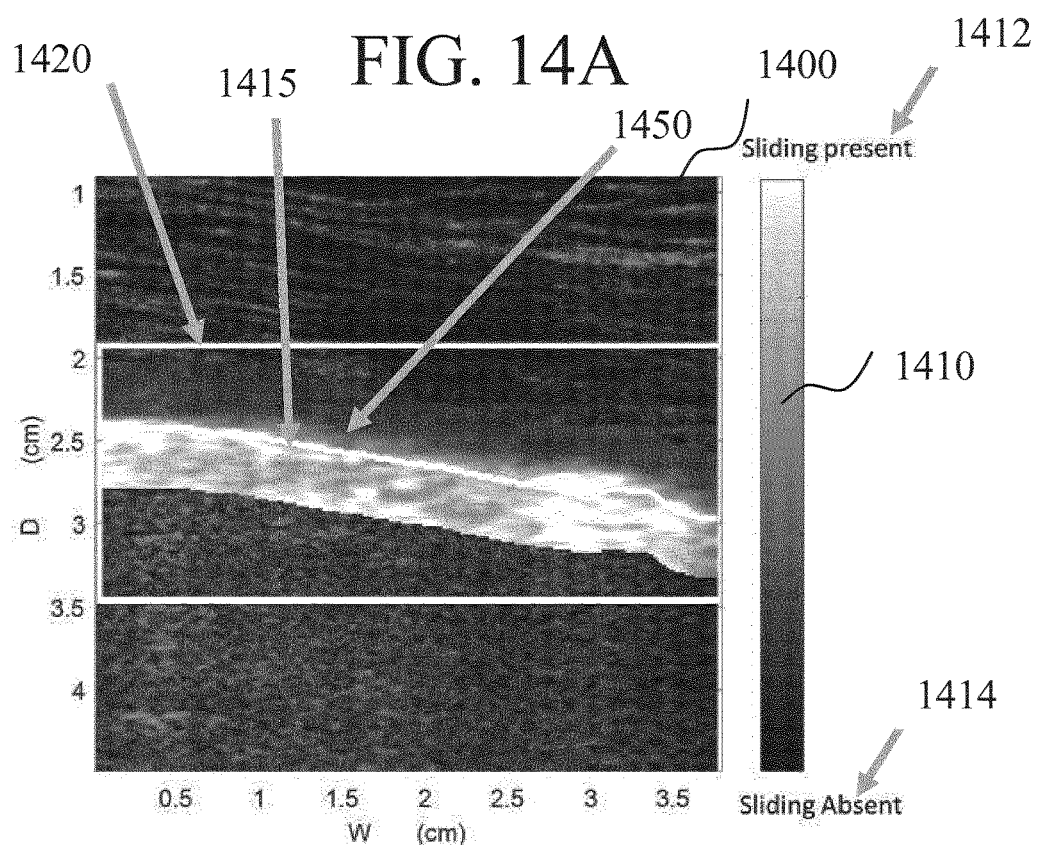
Figure 14C:
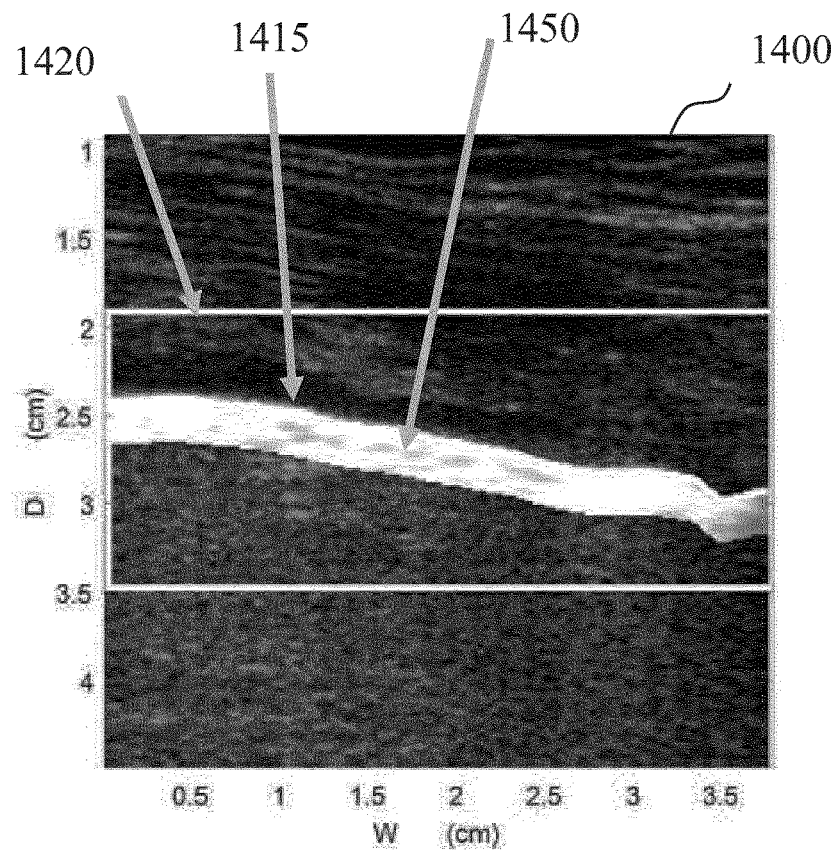
Figure 14D:
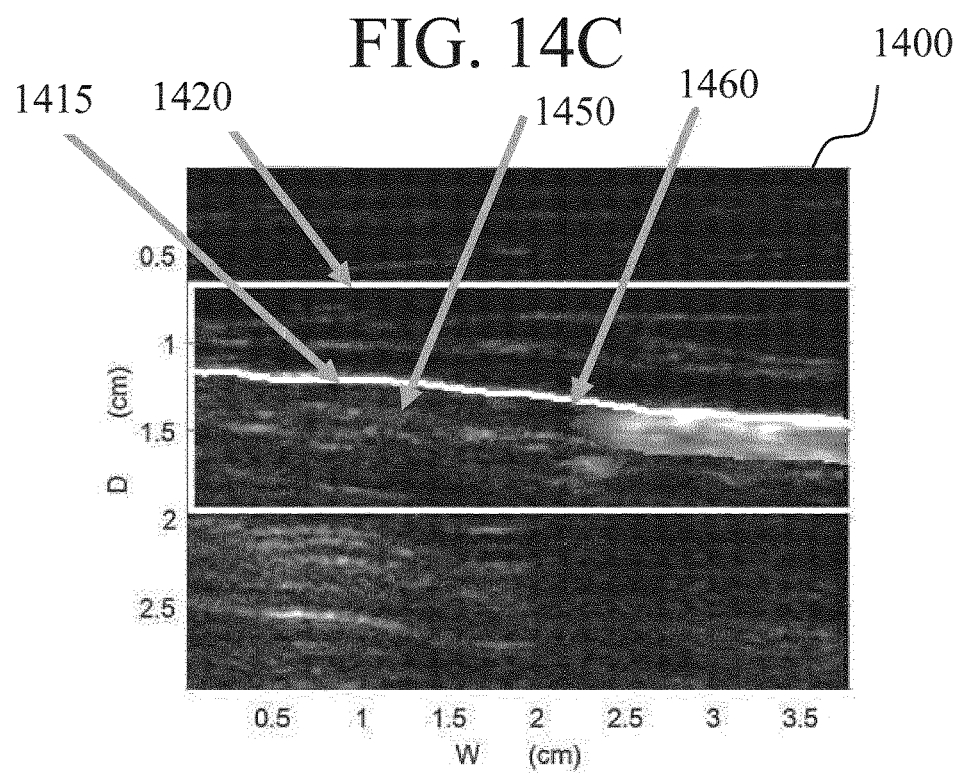
Figure 14E:
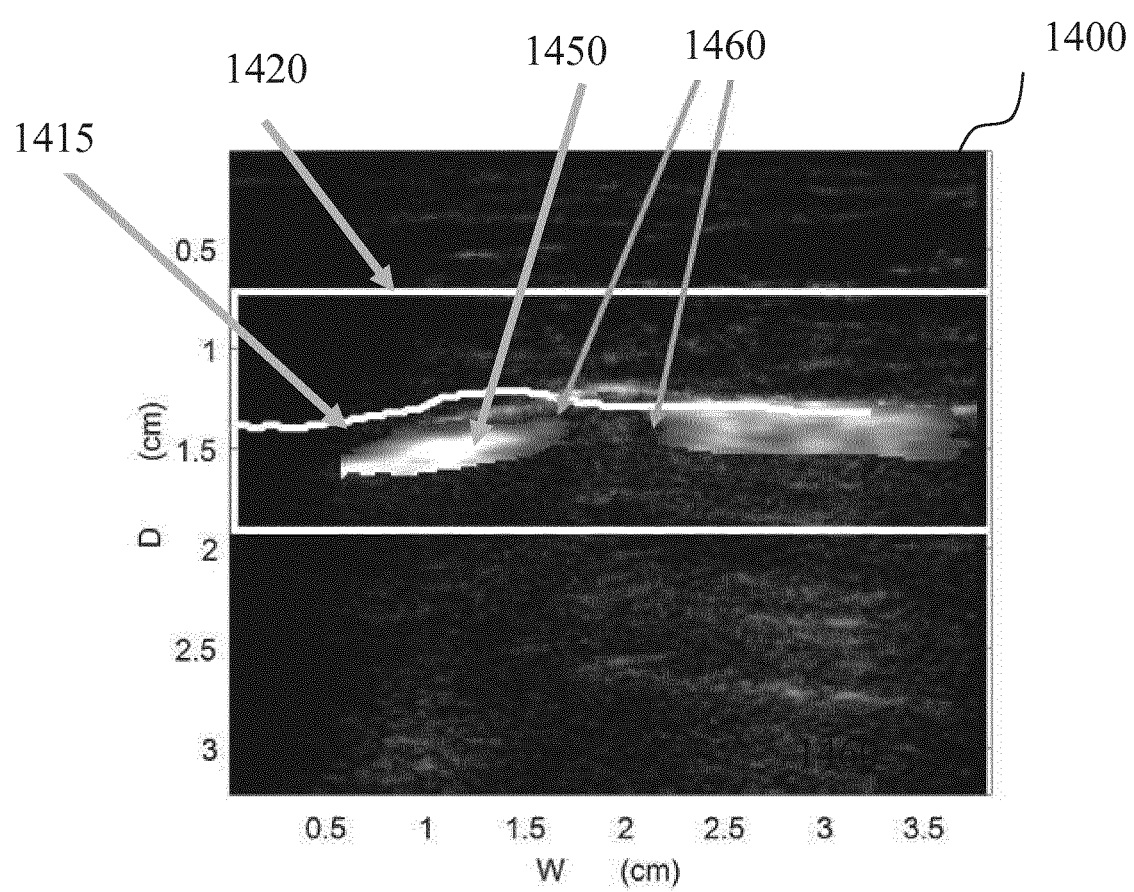
Figure 15:
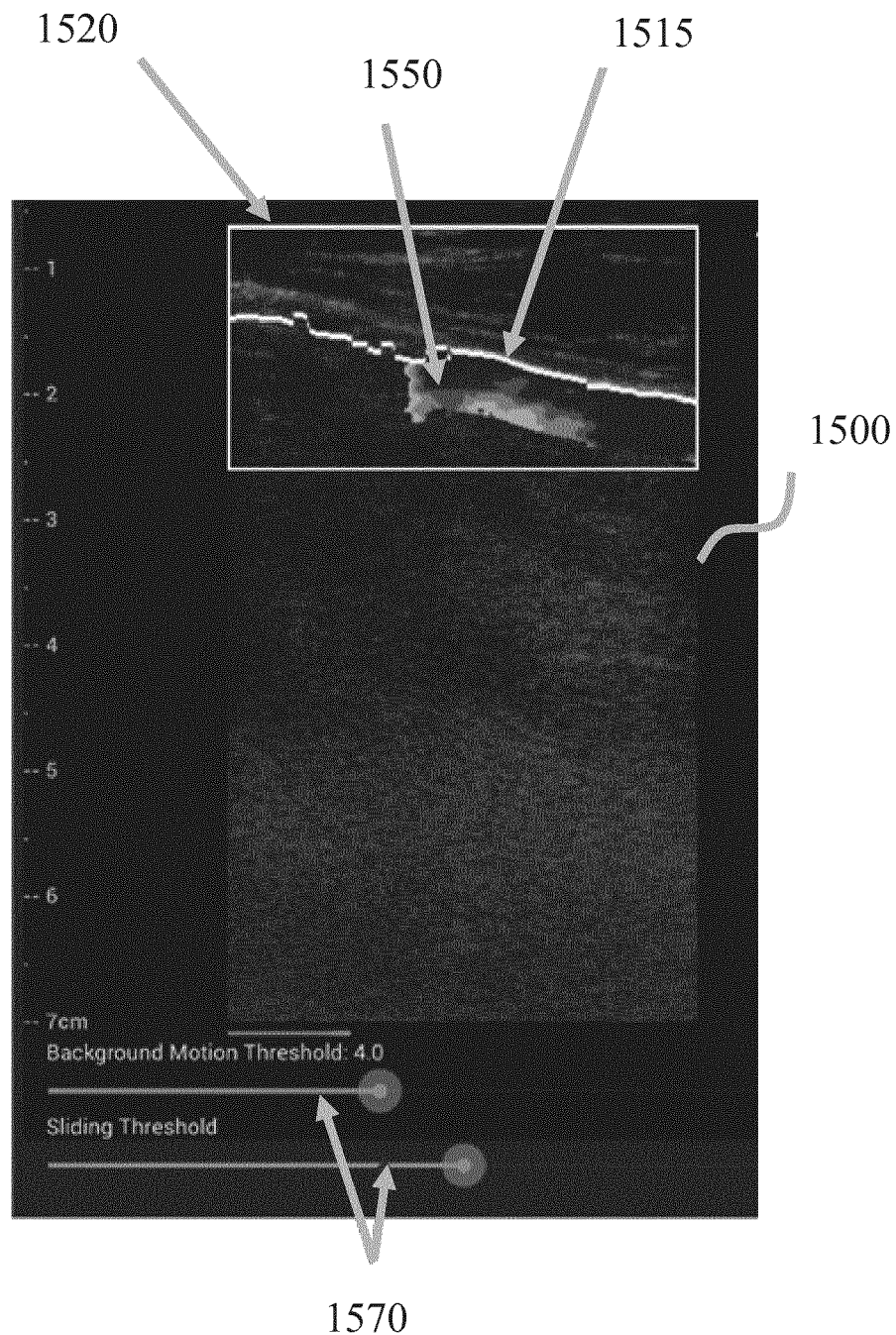
FIG. 15 illustrates an ultrasound B-mode image and two sliding bars for dynamically changing one or more parameters.

FIGS. 14A-14E each illustrate an ultrasound B-mode image 1400 overlaid with a parametric image 1450 for visualizing lung sliding. The bar 1410 is optionally shown and represents the coding scheme of the parametric image 1450. As illustrated in FIG. 14A and FIG. 14B, texts 1412, 1414 can be added to the bar 1410 to indicate the correspondence between the gray-scale and the likelihood of lung sliding. For example, text 1412 "sliding present" on the bright side of the bar and text 1414 "sliding absent" on the dark side show that the likelihood of lung sliding is represented by the brightness, and more particularly, a brighter pixel of the parametric image indicates a higher possibility of presence of sliding. In some other embodiments, a red color is used to indicate the absence of lung sliding, and a blue color is used to indicate the presence of lung sliding, or vice versa. In FIG. 14A, the parametric image 1450 is of the same size as the box 1420 for visualizing the identified sub-region. In FIG. 14B, the parametric image 1450 is in the form of a band encompassing the pleural line 1415, wherein the band follows the trend of the pleural line 1415 and has a fixed size above and below the pleural line 1415. In each of FIGS. 14C-FIG. 14E, the parametric image 1450 is in the form of a band below the pleural line 1415, and the band follows the trend of the pleural line and has a fixed size below the pleural line 1415. FIG. 14C illustrates a normal case where lung sliding is present. FIG. 14D illustrates a single lung point case where lung sliding is partially present and there is a single lung point 1460, and particularly, lung sliding is absent at the left of the lung point 1460, and lung sliding is present at the right of the lung point 1460. FIG. 14E illustrates a double lung point case where lung sliding is partially present and there are two lung points 1460. FIG. 15 illustrates an ultrasound B-mode image 1500 and two sliding bars 1570 for dynamically changing one or more parameters. As illustrated in FIG. 15, the two sliding bars 1570 are displayed below the B-mode image 1500. One sliding bar is used to adjust the predetermined threshold for determining the background motion, and the other sliding bar is used to adjust the predetermined threshold for determining the presence of lung sliding. In FIG. 15, the box 1520 for visualizing the identified sub-region, the line 1515 for visualizing the detected pleural line and the parametric image 1550 are also displayed.

The technique processes described herein may be implemented by various means. For example, these techniques may be implemented in hardware, software, or a combination thereof. For a hardware implementation, the processing units may be implemented within one or more application-specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof. Using software, the implementation can be carried out through modules (e.g., procedures, functions, and so on) that perform the functions described herein. The software codes may be stored in a memory unit and executed by the processors.

Moreover, aspects of the claimed subject matter may be implemented as a method, apparatus, system, or article of manufacture using standard programming and/or engineering techniques to produce software, firmware, hardware, or any combination thereof to control a computer or computing components to implement various aspects of the claimed subject matter. The term "article of manufacture" as used herein is intended to encompass a computer program accessible from any computer-readable device, carrier, or media. For example, computer readable media can include but are not limited to magnetic storage devices (e.g., hard disk, floppy disk, magnetic strips . . . ), optical disks (e.g., compact disk (CD), digital versatile disk (DVD) . . . ), smart cards, and flash memory devices (e.g., card, stick, key drive . . . ). Of course, those skilled in the art will recognize that many modifications may be made to this configuration without departing from the scope or spirit of what is described herein.

As used in this application, the terms "beamformer", "processor" such as "signal processor", "data processor", "identifier", "detector" such as "lung sliding detector", "background motion detector", "pleural line detector", and "estimator" are intended to refer to a processor or a computer-related entity, either hardware, a combination of hardware and software, software, or software in execution. For example, a component may be, but is not limited to, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed among two or more computers.

What has been described above includes examples of one or more embodiments. It is, of course, not possible to describe every conceivable combination of components or methodologies for the purpose of describing the aforementioned embodiments, but one of ordinary skill in the art may recognize that many further combinations and permutations of various embodiments are possible. Accordingly, the described embodiments are intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

The invention claimed is:

1. An apparatus for detecting lung sliding on the basis of a temporal sequence of ultrasound data frames of a first region of interest, the first region of interest including a pleural interface of a lung, the apparatus comprising:
 a data processor configured to:
  identify, for each of at least two ultrasound data frames, a sub-region of a scanned region, the sub-region comprising at least part of the pleural interface;
  derive a parametric map comprising parametric values for the sub-region by extracting data from the sub-region derived from at least two ultrasound data frames of the temporal sequence, the parametric values of the parametric map indicating a degree of tissue motion over the at least two ultrasound frames wherein each parametric value for a pixel location in the sub-region indicates an amount of a change in ultrasound data values of the pixel location over the at least two ultrasound data frames caused by the tissue motion; and
  derive, on the basis of the parametric map, a sliding profile representing sliding values as a function of the likelihood of lung sliding at a lateral position.

2. The apparatus of claim 1, further comprising a user interface configured to visualize the likelihood of lung sliding on the basis of the derived parametric map.

3. The apparatus of claim 2, wherein the user interface is configured to present at least part of the derived parametric map in the form of parametric image, overlaid with an image of at least the sub-region generated on the basis of at least one of the ultrasound data frames of the sequence.

4. The apparatus of claim 2, wherein the user interface is further configured to present the derived sliding profile in the format of a strip, overlaid with or next to an image of at least the sub-region generated on the basis of at least one of the ultrasound data frames of the sequence.

5. The apparatus of claim 2, wherein the user interface is further configured to receive a user input for indicating a modification of the grayscale-coding or color-coding scheme, and to modify the visualization on the basis of the received user input.

6. The apparatus of claim 1, further comprising a user interface configured to receive a user input for indicating a modification to the identified sub-region,
wherein the data processor is further configured to modify the identified sub-region on the basis of the received user input.

7. The apparatus of claim 1, wherein:
the data processor is further configured to detect a pleural line in at least one of the ultrasound data frames; and
wherein the data processor is configured to identify the sub-region for each of the ultrasound data frames on the basis of the detected pleural line.

8. The apparatus of claim 7, wherein the data processor is configured to:
estimate the depth of the pleural interface; and
detect a pleural line in at least one of the ultrasound data frames of the temporal sequence on the basis of the estimated depth.

9. The apparatus of claim 8, wherein the data processor is configured to estimate the depth of the pleural interface by:
deriving, for each of one or more predetermined lateral positions, an intensity profile representing an intensity value as a function of depth, each intensity value indicating an averaged ultrasound data value at the corresponding depth over multiple ultrasound data frames of the temporal sequence, on the basis of the multiple ultrasound data frames of the temporal sequence; and
estimating the depth of the pleural interface on the basis of the derived intensity profile(s).

10. The apparatus of claim 8, wherein the data processor is configured to estimate the depth of the pleural interface by:
receiving an ultrasound data frame of a second region of interest including a pleural interface of the lung and at least one rib, the second region of interest being a transverse view of the lung;
estimating the depth of the at least one rib on the basis of the ultrasound data frame; and
estimating the depth of the pleural interface on the basis of the estimated depth of the at least one rib and a predetermined value.

11. The apparatus of claim 1, wherein:
the data processor is further configured to detect a degree of background motion and determine whether the degree of background motion exceeds a predetermined threshold.

12. The apparatus of 11, wherein the apparatus further comprises a user interface configured to present the derived parametric map only if the degree of background motion does not exceed the predetermined threshold.

13. The apparatus of claim 11, wherein the apparatus further comprises a user interface configured to present an indicator for indicating the degree of background motion if the degree of background motion exceeds the predetermined threshold.

14. An ultrasound system, comprising:
an ultrasound transducer array configured to acquire a temporal sequence of ultrasound data frames of a first region of interest including a pleural interface of a lung; and
a data processor for processing the temporal sequence, configured to:
identify, for each of the ultrasound data frames, a sub-region of a scanned region of the ultrasound data frame, the sub-region comprising at least part of the pleural interface;
extract data from the sub-region identified in each of the at east two ultrasound data frames;
derive a parametric map comprising parametric values for the sub-region on the basis of the extracted data, the parametric values of the parametric map indicating tissue motion over the at least two ultrasound frames, wherein each parametric value for a pixel location in the sub-region indicates an amount of a change in ultrasound data values of the pixel location over the at least two ultrasound data frames caused by the tissue motion; and
derive, on the basis of the parametric map, a sliding profile representing sliding values as a function of lateral position, each sliding value for a lateral position indicating the likelihood of lung sliding at the lateral position.

15. A method of detecting lung sliding, comprising the steps of:
retrieving a temporal sequence of ultrasound data frames of a first region of interest including a pleural interface of a lung;
identifying, for each of the ultrasound data frames, a sub-region of a scanned region of the ultrasound data frame, the sub-region comprising at least part of the pleural interface;
extracting data from the sub-region identified in each of the at least two ultrasound data frames;
deriving a parametric map comprising parametric values for the sub-region on the basis of the extracted data, the parametric values of the parametric map indicating tissue motion over the at least two ultrasound frames, wherein each parametric value for a pixel location in the sub-region indicates an amount of a change in ultrasound data values of the pixel location over the at least two ultrasound data frames caused by the tissue motion; and
deriving, on the basis of the parametric map, a sliding profile representing sliding values as a function of lateral position, each sliding value for a lateral position indicating the likelihood of lung sliding at the lateral position.

16. A non-transitory computer readable medium comprising computer program instructions which, when being executed by a computing device, cause the computing device to perform the method of claim 15.

* * * * *